(12) United States Patent
Schmidtler et al.

(10) Patent No.: US 7,958,067 B2
(45) Date of Patent: *Jun. 7, 2011

(54) DATA CLASSIFICATION METHODS USING MACHINE LEARNING TECHNIQUES

(75) Inventors: Mauritius A. R. Schmidtler, Escondido, CA (US); Roland Borrey, Villa Park, CA (US); Anthony Sarah, San Diego, CA (US)

(73) Assignee: Kofax, Inc., Irvine, CA (US)

( * ) Notice: Subject to any disclaimer, the term of this patent is extended or adjusted under 35 U.S.C. 154(b) by 651 days.

This patent is subject to a terminal disclaimer.

(21) Appl. No.: 11/752,673

(22) Filed: May 23, 2007

(65) Prior Publication Data
US 2008/0082352 A1 Apr. 3, 2008

Related U.S. Application Data

(60) Provisional application No. 60/830,311, filed on Jul. 12, 2006.

(51) Int. Cl.
*G06F 15/18* (2006.01)
(52) U.S. Cl. ............... 706/20; 706/12; 706/15
(58) Field of Classification Search .......... 706/12, 706/15, 20, 21, 45, 52, 62
See application file for complete search history.

(56) References Cited

U.S. PATENT DOCUMENTS

| | | | | |
|---|---|---|---|---|
| 5,159,667 A | 10/1992 | Borrey et al. | | 395/148 |
| 6,192,360 B1 | 2/2001 | Dumais et al. | | 707/6 |
| 6,327,581 B1 | 12/2001 | Platt | | 706/12 |
| 6,370,277 B1 | 4/2002 | Borrey et al. | | 82/260 |
| 6,463,430 B1 | 10/2002 | Brady et al. | | 707/3 |
| 6,633,857 B1 * | 10/2003 | Tipping | | 706/16 |
| 7,184,929 B2 | 2/2007 | Goodman | | 702/181 |
| 7,340,376 B2 | 3/2008 | Goodman | | 702/181 |
| 7,366,705 B2 | 4/2008 | Zeng et al. | | 706/20 |
| 7,562,060 B2 * | 7/2009 | Sindhwani et al. | | 706/25 |
| 2002/0165717 A1 | 11/2002 | Solmer et al. | | 704/256 |
| 2003/0101161 A1 * | 5/2003 | Ferguson et al. | | 707/1 |
| 2003/0120653 A1 | 6/2003 | Brady et al. | | 707/7 |
| 2004/0111453 A1 | 6/2004 | Harris et al. | | 708/200 |
| 2005/0134935 A1 | 6/2005 | Schmidtler et al. | | 358/448 |
| 2005/0216426 A1 | 9/2005 | Weston et al. | | 706/12 |
| 2005/0234955 A1 * | 10/2005 | Zeng et al. | | 707/101 |
| 2005/0265618 A1 * | 12/2005 | Jebara | | 382/243 |
| 2006/0093208 A1 * | 5/2006 | Li et al. | | 382/159 |
| 2006/0120609 A1 * | 6/2006 | Ivanov et al. | | 382/224 |
| 2006/0235812 A1 * | 10/2006 | Rifkin et al. | | 706/14 |
| 2007/0005341 A1 | 1/2007 | Burges et al. | | 704/9 |
| 2007/0239642 A1 * | 10/2007 | Sindhwani et al. | | 706/25 |

OTHER PUBLICATIONS

Joachims, "Transductive Learning Via Spectral Graph Partitioning", ICML, 2003, pp. 1-8.*
Joachims, "Transductive Interference for Text Classification using Support Vector Machines", 1999, pp. 1-10.*
Jaakoba et al., "MAximum Entropy Discrimination", 1999, pp. 1-26.*
Notice of Allowance from U.S. Appl. No. 10/412,613 mailed on Mar. 25, 2008.

(Continued)

*Primary Examiner* — Omar F Fernandez Rivas
(74) *Attorney, Agent, or Firm* — Zilka-Kotab, PC

(57) ABSTRACT

Methods for classifying documents are presented. Methods for analyzing documents associated with legal discovery are also presented. Methods for cleaning up data are also presented. Methods for verifying an association of an invoice with an entity are also presented. Method for managing medical records are presented. Method for face recognition are presented.

31 Claims, 29 Drawing Sheets

OTHER PUBLICATIONS

Office Action Summary from U.S. Appl. No. 11/752,691 mailed on Feb. 24, 2010.

Nigam, Using Unlabeled Data to Improve Text Classification, Doctoral Thesis, Carnegie Mellon University, 2001, pp. 1-128.

Office Action Summary from U.S. Appl. No. 11/752,719 mailed on Nov. 30, 2009.

Thorsten, Joachims, "Transducive Interference for Text Classification Using Support Vector Machines", Proceedings of the International Conference on Machine Learning (ICML), 1999, pp. 1-10.

Jebara et al., "Feature Selection and Dualities in Maximum Entropy Discrimination", 16$^{th}$ Conference on Uncertainty in Artificial Intelligence, UAI 2000. Jul. 2000, pp. 1-10.

Chen et al., "Learning with Progressive Transductive Support Vector Machines", 2003, pp. 1845-1855.

U.S. Appl. No. 11/752,634, filed May 23, 2007.

U.S. Appl. No. 11/752,691, filed May 23, 2007.

U.S. Appl. No. 11/752,719, filed May 23, 2007.

Jaakkola et al., "Maximum entropy discrimination" Aug. 18, 1990, Revised Oct. 10, 1999, pp. 1-26.

Office Action Summary from U.S. Appl. No. 10/412,163 mailed on Oct. 25, 2007.

"The American Heritage College Dictionary; Fourth Edition"—definition of "relationship". 2004., p. 1173.

Rennie, J.D. et al., "Improving Multiclass Text Classification With The Support Vector Machine". Oct. 2001., pp. 1-14.

Kolcz, A. et al., "Summarization As Feature Selection For Text Categorization" CIKM '01 Nov. 2001, pp. 365-370.

Cristianini, N. et al., "An Introduction To Support Vector Machines And Other Kemel-Based Learning Methods" pp. 8-11, 26-41, 92-101, 124-129. 2000.

Kindermann, J. et al., "Error Correcting Codes With Optimized Kullback-Leibler Distances for Text Categorization". PKDD 2001. Springer-Verlag 2001, pp. 276-276.

Russell, S. et al., "Artificial Intelligence: A Modern Approach; Second Edition"—(§20.6) pp. 749-752. 2003.

Platt et al., "Large Margin DAGs for Multiclass Classification" Advances in Neural Information Processing Systems 12, pp. 547-553, MIT Press. 2000.

Drucker, H. et al., "Support Vector Machines for Spam Categorization" IEEE. Sep. 1999., pp. 1048-1054.

Weston, J. et al., "Support Vector Machines for Multi-Class Pattern Recognition" Proceedings of the Seventh European Symposium on Artificial Neural Networks. 1999., 6 pages.

Fragoudis, D. et al., "Integrating Feature and Instance Selection for Text Classification" SIGKDD'02. ACM. Jul. 2002, pp. 501-506.

Final Office Action Summary from U.S. Appl. No. 11/752,691 mailed on Sep. 3, 2010.

Final Office Action Summary from U.S. Appl. No. 11/752,719 mailed on May 28, 2010.

Notice of Allowance from U.S. Appl. No. 11/752,719 dated Dec. 28, 2010.

\* cited by examiner

DATA CLASSIFICATION METHODS USING MACHINE LEARNING TECHNIQUES

CROSS-REFERENCE TO RELATED APPLICATIONS

This application claims priority to U.S. Provisional Patent Application Ser. No. 60/830,311, filed Jul. 12, 2006, which is herein incorporated by reference.

FIELD OF THE INVENTION

The present invention relates generally to methods and apparatus for data classification. More particularly, the present invention relates to novel applications using machine learning techniques.

BACKGROUND

How to handle data has gained in importance in the information age and more recently with the explosion of electronic data in all walks of life including, among others, scanned documents, web material, search engine data, text data, images, audio data files, etc.

One area just starting to be explored is the non-manual classification of data. In many classification methods the machine or computer must learn based upon manually input and created rule sets and/or manually created training examples. In machine learning where training examples are used, the number of learning examples is typically small compared to the number of parameters that have to be estimated, i.e. the number of solutions that satisfy the constraints given by the training examples is large. A challenge of machine learning is to find a solution that generalizes well despite the lack of constraints. There is thus a need for overcoming these and/or other issues associated with the prior art.

What is further needed are practical applications for machine learning techniques of all types.

SUMMARY

A method for classifying documents according to one embodiment of the present invention includes receiving at least one labeled seed document having a known confidence level of label assignment; receiving unlabeled documents; receiving at least one predetermined cost factor; training a transductive classifier through iterative calculation using the at least one predetermined cost factor, the at least one seed document, and the unlabeled documents, wherein for each iteration of the calculations the cost factor is adjusted as a function of an expected label value; after at least some of the iterations, storing confidence scores for the unlabeled documents; and outputting identifiers of the unlabeled documents having the highest confidence scores to at least one of a user, another system, and another process.

A method for analyzing documents associated with legal discovery according to another embodiment of the present invention includes receiving documents associated with a legal matter; performing a document classification technique on the documents; and outputting identifiers of at least some of the documents based on the classification thereof.

A method for cleaning up data according to another embodiment of the present invention includes receiving a plurality of labeled data items; selecting subsets of the data items for each of a plurality of categories; setting an uncertainty for the data items in each subset to about zero; setting an uncertainty for the data items not in the subsets to a predefined value that is not about zero; training a transductive classifier through iterative calculation using the uncertainties, the data items in the subsets, and the data items not in the subsets as training examples; applying the trained classifier to each of the labeled data items to classify each of the data items; and outputting a classification of the input data items, or derivative thereof, to at least one of a user, another system, and another process.

A method for verifying an association of an invoice with an entity according to another embodiment of the present invention includes training a classifier based on an invoice format associated with a first entity; accessing a plurality of invoices labeled as being associated with at least one of the first entity and other entities; performing a document classification technique on the invoices using the classifier; and outputting an identifier of at least one of the invoices having a high probability of not being associated with the first entity.

A method for managing medical records according to another embodiment of the present invention includes training a classifier based on a medical diagnosis; accessing a plurality of medical records; performing a document classification technique on the medical records using the classifier; and outputting an identifier of at least one of the medical records having a low probability of being associated with the medical diagnosis.

A method for face recognition according to another embodiment of the present invention includes receiving at least one labeled seed image of a face, the seed image having a known confidence level; receiving unlabeled images; receiving at least one predetermined cost factor; training a transductive classifier through iterative calculation using the at least one predetermined cost factor, the at least one seed image, and the unlabeled images, wherein for each iteration of the calculations the cost factor is adjusted as a function of an expected label value; after at least some of the iterations, storing confidence scores for the unlabeled seed images; and outputting identifiers of the unlabeled images having the highest confidence scores to at least one of a user, another system, and another process.

DETAILED DESCRIPTION

Figure 1:
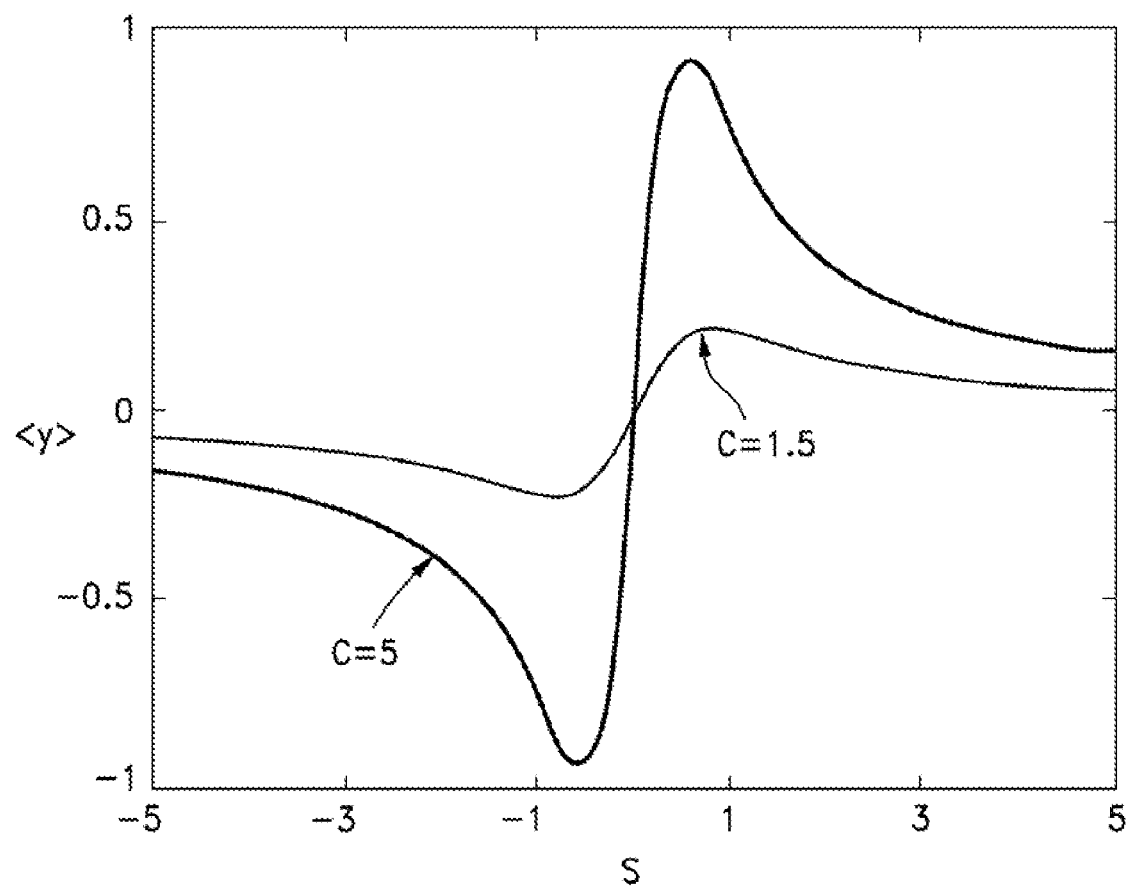
FIG. 1 is a depiction of a chart plotting the expected label as a function of the classification score as obtained by employing MED discriminative learning applied to label induction.
Figure 2A:
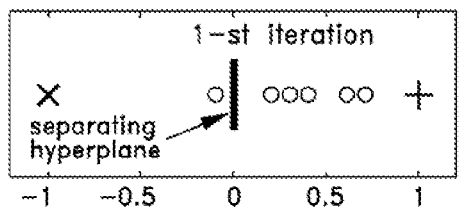
FIG. 2 is a depiction of a series of plots showing calculated iterations of the decision function obtained by transductive MED learning.
Figure 2B:
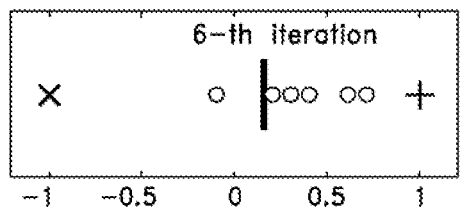
Figure 2C:
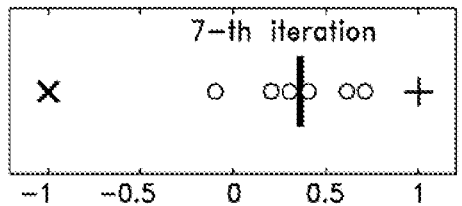
Figure 2D:
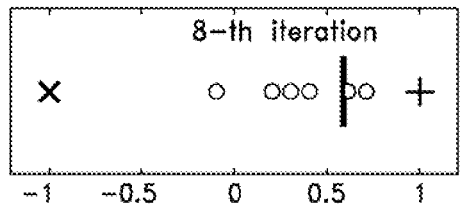
Figure 2E:
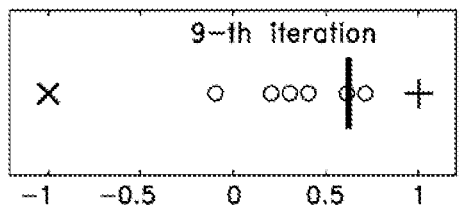
Figure 2F:
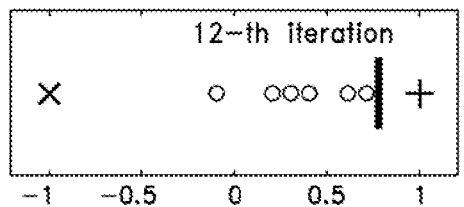
Figure 2G:
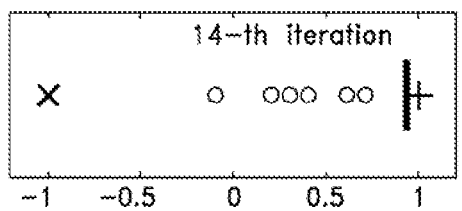
Figure 2H:
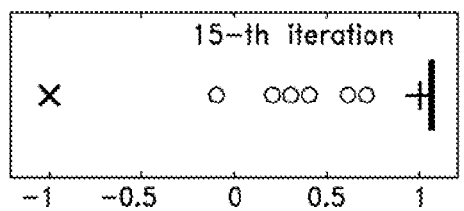
Figure 3A:
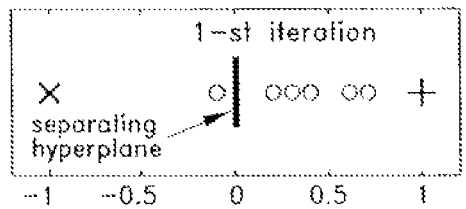
FIG. 3 is depiction of a series of plots showing calculated iterations of the decision function obtained by the improved transductive MED learning of one embodiment of the present invention.
Figure 3B:
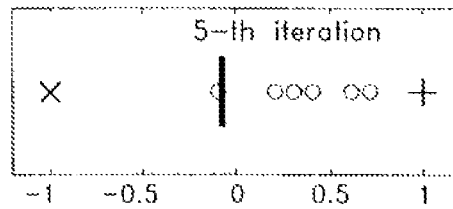
Figure 3C:
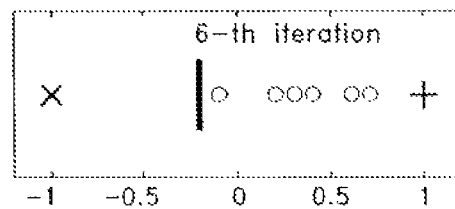
Figure 3D:
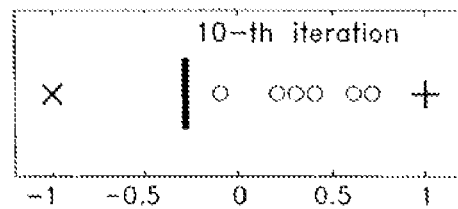
Figure 3E:
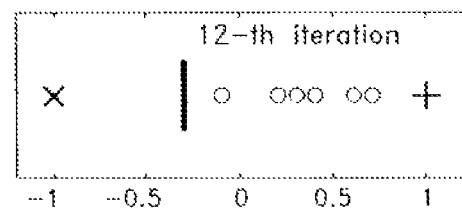
Figure 3F:
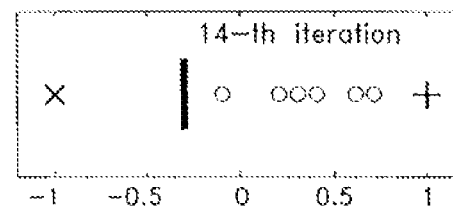
Figure 3G:
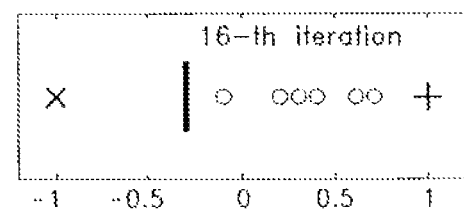
Figure 3H:
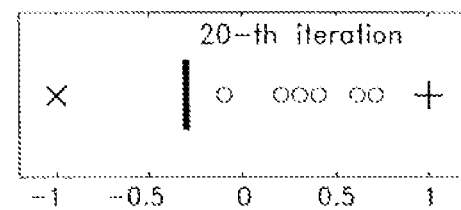

The following description is the best mode presently contemplated for carrying out the present invention. This description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and as defined in dictionaries, treatises, etc.

The interest and need for classification of textual data has been particularly strong, and several methods of classification have been employed. A discussion of classification methods for textual data is described in U.S. Pat. No. 6,192,360 to Dumais, the content and substance of which is incorporated herein by reference.

The current state of the art in commercially used automatic classification systems is either rule based or utilizes inductive machine learning, i.e. using manually labeled training examples. Both methods typically entail a large manual setup effort compared to transductive methods. The solutions provided by rule based systems or inductive methods are static solutions that cannot adapt to drifting classification concepts without manual effort.

Inductive machine learning is used to ascribe properties or relations to types based on tokens (i.e., on one or a small number of observations or experiences); or to formulate laws based on limited observations of recurring patterns. Inductive machine learning involves reasoning from observed training cases to create general rules, which are then applied to the test cases. Particularly, preferred embodiments use transductive machine learning techniques. Transductive machine learning is a powerful method that does not suffer from these disadvantages.

Transductive machine techniques may be capable of learning from a very small set of labeled training examples, automatically adapting to drifting classification concepts, and automatically correcting the labeled training examples. These advantages make transductive machine learning an interesting and valuable method for a large variety of commercial applications.

Transduction learns patterns in data. It extends the concept of inductive learning by learning not only from labeled data but also from unlabeled data. This enables transduction to learn patterns that are not or only partly captured in the labeled data. As a result transduction can, in contrast to rule based systems or systems based on inductive learning, adapt to dynamically changing environments. This capability enables transduction to be utilized for document discovery, data cleanup, and addressing drifting classification concepts, among other things.

The following is an explanation of one embodiment of transductive classification utilizing Support Vector Machine (SVM) classification as well as the Maximum Entropy Discrimination (MED) framework.

Support Vector Machines

Support Vector Machines (SVM) is one employed method of text classification, and such method approaches the problem of the large number of solutions and the resulting generalization problem by deploying constraints on the possible solutions utilizing concepts of regularization theory. For example, a binary SVM classifier selects from all hyperplanes that separate the training data correctly as solution the hyperplane that maximizes the margin. The maximum margin regularization under the constraint that training data is classified correctly addresses the aforementioned learning problem of selecting the appropriate trade-off between generalization and memorization: The constraint on the training data memorizes the data, whereas the regularization ensures appropriate generalization. Inductive classification learns from training examples that have known labels, i.e. every training example's class membership is known. Where inductive classification learns from known labels, transductive classification determines the classification rules from labeled as well as unlabeled data. An example of transductive SVM classification is shown in table 1.

Principle of Transductive SVM Classification

Require: Data matrix X of labeled training examples and their labels Y.

Require: Data matrix X' of the unlabeled training
examples.
Require: A list of all possible labels assignments of the
unlabeled training examples $[Y'_1, \ldots, Y'_n]$.

TABLE 1

1: MaximumMargin = 0
2: $\hat{Y}$ = 0 {Included label assignment of unlabeled training examples.}
3: for all label assignments $Y'_i$, $1 \leq i \leq n$ in the list of label assignments
do
4:    CurrentMaximumMargin := MaximizeMargin(X,Y,X',$Y'_i$)
5:    if CurrentMaximumMargin > MaximumMargin then
6:        MaximumMargin := CurrentMaximumMargin
7:        $\hat{Y} := Y'_i$
8:    end if
9: end for Table 1 shows the principle of a transductive classification with Support Vector Machines: The solution is given by the hyperplane that yields the maximum margin over all possible label assignments of the unlabeled data. The possible label assignments grow exponentially in the number of unlabeled data and for practically applicable solutions, the algorithm in Table 1 must be approximated. An example of such an approximation is described in T. Joachims, *Transductive inference for text classification using support vector machines*, Technical report, Universitaet Dortmund, LAS VIII, 1999 (Joachims).

The uniform distribution over label assignments in Table 1 implies that an unlabeled data point has a probability of ½ to be a positive example of the class and a probability of ½ of being a negative example, i.e. its two possible label assignments of y=+1 (positive example) and y=−1 (negative example) are equally likely and the resulting expected label is zero. A label expectation of zero can be obtained by a fixed class prior probability equal to ½ or a class prior probability that is a random variable with an uniform prior distribution, i.e. an unknown class prior probability. Accordingly, in applications with known class prior probabilities that are not equal to ½ the algorithm could be improved by incorporating this additional information. For example, instead of using a uniform distribution over label assignments in Table 1, one could elect to prefer some label assignments over others according to the class prior probability. However, the trade-off between a smaller margin solution with a likely label assignment and a higher margin solution but less likely label assignment is difficult. The probability of label assignments and the margin are on different scales.

Maximum Entropy Discrimination

Another method of classification, Maximum Entropy Discrimination (MED) (see e.g. T. Jebara, *Machine Learning Discriminative and Generative*, Kluwer Academic Publishers) (Jebara) does not encounter the problems associated with SVMs since the decision function regularization term as well as the label assignment regularization term are both derived from prior probability distributions over solutions and, thus are both on the same probabilistic scale. Accordingly, if the class priors and, thus, the label priors are known, transductive MED classification is superior to transductive SVM classification, since it allows for the incorporation of prior label knowledge in a principled way.

Inductive MED classification assumes a prior distribution over the parameters of the decision function, a prior distribution over the bias term, and a prior distribution over margins. It selects as a final distribution over these parameters the one that is closest to the prior distributions and yields an expected decision function that classifies the data points correctly.

Formally, for example given a linear classifier, the problem is formulated as follows: Find the distribution over hyperplane parameters $p(\Theta)$, the bias distribution $p(b)$, the data points classification margins $p(\gamma)$ whose combined probability distribution has a minimal Kullback Leibler divergence KL to the combined respective prior distributions $p_0$, i.e.

$$\min_{p(\Theta)p(\gamma)p(b)} = KL(p(\Theta)p(\gamma)p(b) \| p_0(\Theta)p_0(\gamma)p_0(b)), \quad (1)$$

subject to the constraint $$\forall t: \int d\Theta d\gamma db p(\Theta)p(\gamma)p(b)(y_t(\Theta X_t-b))-y_t) \geq 0, \quad (2)$$

where the $\Theta X_t$ is the dot product between the separating hyperplane's weight vector and the t-th data point's feature vector. Since the label assignments $y_t$ are known and fixed, no prior distribution over the binary label assignments is needed. Accordingly, a straightforward method to generalize inductive MED classification to transductive MED classification is to treat the binary label assignments as parameters that are constrained by a prior distribution over possible label assignments. An example of transductive MED is shown in Table 2.

Transductive MED Classification
Require: Data Matrix X of labeled and unlabeled training examples.
Require: Label prior probabilities $p_0(y)$ for labeled and unlabeled training examples.

TABLE 2

1:    $\langle Y \rangle$ := ExpectedLabel($p_o(y)$) {Expected label determined from the training examples' label prior probabilities.}
2:    while ¬converged do
3:        W := MinimizeKLDivergence(X,$\langle Y \rangle$)
4:        Y' := InduceLables(W,X,$p_o(y)$)
5:        $\langle Y \rangle := \epsilon \langle Y \rangle + (1-\epsilon)Y'$
6:    end while For the labeled data, the label prior distribution is a $\delta$ function, thus, effectively fixing the label to be either +1 or −1. For the unlabeled data, a label prior probability $p_0(y)$ is assumed that assigns to every unlabeled data point a positive label of y=+1 with a probability of $p_0(y)$ and a negative label of y=−1 with a probability of $1-p_0(y)$. Assuming a noninformative label prior ($p_0(y)=\frac{1}{2}$), yields a transductive MED classification analogous to the transductive SVM classification discussed above.

As in the case of the transductive SVM classification, a practically applicable implementation of such an MED algorithm must approximate the search through all possible label assignments. The method described in T. Jaakkola, M. Meila, and T. Jebara, *Maximum entropy discrimination*, Technical Report AITR-1668, Massachusetts institute of Technology, Artificial Intelligence Laboratory, 1999 (Jaakkola) elects as an approximation to decompose the procedure into two steps, similar to an Expectation Maximization (EM) formulation. In this formulation, there are two problems to solve. The first, analogous to the M step in EM algorithms, is similar to the maximization of the margin while classifying all data points correctly according to the current best guess of label assignments. The second step, analogous to the E step, uses the classification results determined in the M step and estimates new values for each example's class membership. This second step we call label induction. A general description is shown in Table 2.

The specific implementation of the method of Jaakkola, referenced herein, assumes a Gaussian with zero mean and unit variance for the hyperplane parameters, a Gaussian with zero mean and variance $\sigma_b^2$ for the bias parameter, a margin prior of the form $\exp[-c(1-\gamma)]$ with $\gamma$ a data point's margin and c the cost factor, and a binary label prior probability of $p_0(y)$ for unlabeled data as discussed above. For the following discussion of the transductive classification algorithm Jaakkola, referenced herein, a label prior probability of ½ is assumed for reasons of simplicity and without loss of generality.

The label induction step determines the label probability distribution given a fixed probability distribution for the hyperplane parameters. Using the margin and label priors introduced above yields the following objective function for the label induction step (see Table 2)

$$\mathfrak{J}(\lambda) = \sum_t (\lambda_t + \log(1 - \lambda_t/c)) - \log\cosh(\lambda_t s_t), \quad (3)$$

where $\lambda_t$ is the t-th training example Lagrange Multiplier, and $s_t$ its classification score determined in the previous M-step, and c the cost factor. The first two terms in the sum over the training examples is derived from the margin prior distribution, whereas the third term is given by the label prior distribution. By maximizing $\mathfrak{J}$ the Lagrange Multipliers are determined and, thus, the label probability distributions for the unlabeled data. As can be seen from Eq. 3 the data points contribute independently to the objective function and, thus, each Lagrange Multiplier can be determined irrespective of every other Lagrange Multiplier. For example, in order to maximize the contribution of an unlabeled data point with a high absolute value of its classification score $|s_t|$ a small Lagrange Multiplier $\lambda_t$ is required, whereas an unlabeled data point with a small value of $|s_t|$ maximizes its contribution to $\mathfrak{J}$ with a large Lagrange Multiplier. On the other hand, the expected label $\langle y \rangle$ of an unlabeled data point as a function of its classification score s and its Lagrange Multiplier $\lambda$ is $$\langle y \rangle = \tan h(\lambda s). \quad (4)$$

FIG. 1 shows the expected label $\langle y \rangle$ as a function of the classification score s using the cost factor of c=5 and c=1.5. The Lagrange Multipliers used in the generation of FIG. 1 have been determined by solving Eq. 3 using a cost factor of c=5 and c=1.5. As can be seen from FIG. 1, unlabeled data points outside the margin, i.e. $|s|>1$ have expected labels $\langle y \rangle$ close to zero, data points close to the margin, i.e. $|s|\approx 1$, yield the highest absolute expected label values, and data points close to the hyperplane, i.e. $|s|<\epsilon$, yield $|\langle y \rangle|<\epsilon$. The reason for this unintuitive label assignment of $\langle y \rangle \rightarrow 0$ for $|s|\rightarrow\infty$ lies within the elected discriminative approach that attempts to stay as close as possible to the prior distribution as long as the classification constraints are fulfilled. It is not an artifact of the approximation elected by the known method of Table 2, i.e. an algorithm that exhaustively searches through all possible label assignments and, thus, has the guarantee to find the global optimum also assigns unlabeled data outside the margin expected labels either close to or equal to zero. Again, as mentioned above, that is expected from a discriminative point of view. Data points outside the margin are not important for separating the examples and, thus, all individual probability distributions of these data points revert back to their prior probability distribution.

The M step of the transductive classification algorithm of Jaakkola, referenced herein, determines the probability distributions for the hyperplane parameters, the bias term, and margins of the data points that are closest to the respective prior distribution under the constraints $$\forall t: s_t \langle y_t \rangle - \langle \gamma_t \rangle \geq 0, \quad (5)$$

where $s_t$ is the t-th data point classification score, $\langle y_t \rangle$ its expected label and $\langle \gamma_t \rangle$ its expected margin. For labeled data, the expected label is fixed and either $\langle y \rangle = +1$ or $\langle y \rangle = -1$. The expected label for unlabeled data lies in the interval $(-1, +1)$ and is estimated in the label induction step. According to Eq. 5 unlabeled data have to fulfill tighter classification constraints than labeled data since the classification score is scaled by the expected label. Furthermore, given the dependence of the expected label as a function of the classification score, referring to FIG. 1, unlabeled data close to the separating hyperplane have the most stringent classification constraints since their score as well as the absolute value of their expected label $|\langle y_t \rangle|$ is small. The M step's full objective function given the prior distributions mentioned above is $$\mathfrak{J}(\lambda) = -\frac{1}{2}\sum_{t,t'} \langle y_t \rangle\langle y_{t'} \rangle\lambda_t\lambda_{t'} K(X_t, X_{t'}) + \qquad (6)$$

$$\sum_t (\lambda_t + \log(1 - \lambda_t/c)) - \frac{1}{2}\left(\sigma_b \sum_t \langle y_t \rangle\lambda_t\right)^2.$$

The first term is derived from the Gaussian hyperplane parameters prior distribution, the second term is the margin prior regularization term and the last term is the bias prior regularization term derived from a Gaussian prior with zero mean and variance $\sigma_b^2$. The prior distribution over the bias term can be interpreted as a prior distribution over class prior probabilities. Accordingly, the regularization term that corresponds to the bias prior distribution constrains the weight of the positive to negative examples. According to Eq. 6, the contribution of the bias term is minimized in case the collective pull of the positive examples on the hyperplane equals the collective pull of the negative examples. The collective constraint on the Lagrange Multipliers owing to the bias prior is weighted by the expected label of the data points and is, therefore, less restrictive for unlabeled data than for labeled data. Thus, unlabeled data have the ability of influencing the final solution stronger than the labeled data.

In summary, at the M step of the transductive classification algorithm of Jaakkola, referenced herein, unlabeled data have to fulfill stricter classification constraints than the labeled data and their cumulative weight to the solution is less constrained than for labeled data. In addition, unlabeled data with an expected label close to zero that lie within the margin of the current M step influence the solution the most. The resulting net effect of formulating the E and M step this way is illustrated by applying this algorithm to the dataset shown in FIG. 2. The dataset includes two labeled examples, a negative example (x) at x-position −1 and a positive example (+) at +1, and six unlabeled examples (o) between −1 and +1 along the x-axis. The cross (x) denotes a labeled negative example, the plus sign (+) a labeled positive example, and the circles (o) unlabeled data. The different plots show separating hyperplanes determined at various iterations of the M step. The final solution elected by the transductive MED classifier of Jaakkaola, referenced herein, misclassifies the positive labeled training example. FIG. 2 shows several iterations of the M step. At the first iteration of the M step, no unlabeled data are considered and the separating hyperplane is located a x=0. The one unlabeled data point with a negative x-value is closer than any other unlabeled data to this separating hyperplane. At the following label induction step, it will get assigned the smallest |⟨y⟩| and, accordingly, at the next M step it has the most power to push the hyperplane towards the positive labeled example. The specific shape of the expected label ⟨y⟩ as a function of the classification score determined by the chosen cost factor (see FIG. 1) combined with the particular spacing of the unlabeled data points creates a bridge effect, where at each consecutive M step the separating hyperplane is moving closer and closer towards the positive labeled example. Intuitively, the M step suffers from a kind of short sightedness, where the unlabeled data point closest to the current separating hyperplane determines the final position of the plane the most and the data points further away are not very important. Finally, owing to the bias prior term that restricts the collective pull of unlabeled data less than the collective pull of the labeled data, the separating hyperplane moves beyond the positive labeled example yielding a final solution, 15-th iteration in FIG. 2, that misclassifies the positive labeled example. A bias variance of $\sigma_b^2 = 1$ and a cost factor of c=10 has been used in FIG. 2. With $\sigma_b^2 = 1$ any cost factor in the range 9.8<c<13 results in a final hyperplane that misclassifies the one positive labeled example. Cost factors outside the interval 9.8<c<13 yield separating hyperplanes anywhere between the two labeled examples.

This instability of this algorithm is not restricted to the example shown in FIG. 2, but also has been experienced while applying the Jaakkola method, referenced herein, to real world datasets, involving the Reuters data set known to those skilled in the art. The inherent instability of the method described in Table 2 is a major shortcoming of this implementation and restricts its general usability, though the Jaakkola method may be implemented in some embodiments of the present invention.

One preferred approach of the present invention employs transductive classification using the framework of Maximum Entropy Discrimination (MED). It should be understood that various embodiments of the present invention, while applicable for classification may also be applicable to other MED learning problems using transduction, including, but not limited to transductive MED regression and graphical models.

Maximum Entropy Discrimination constrains and reduces the possible solutions, by assuming a prior probability distribution over the parameters. The final solution is the expectation of all possible solutions according to the probability distribution that is closest to the assumed prior probability distribution under the constraint that the expected solution describes the training data correctly. The prior probability distribution over solutions maps to a regularization term, i.e. by choosing a specific prior distribution one has selected a specific regularization.

Discriminative estimation as applied by Support Vector Machines is effective in learning from few examples. This method and apparatus of one embodiment of the present invention has this in common with Support Vector Machines and does not attempt to estimate more parameters than necessary for solving the given problem and, consequently, yields a sparse solution. This is in contrast to generative model estimation that attempts to explain the underlying process and, in general needs higher statistics than discriminative estimation. On the other hand, generative models are more versatile and can be applied to a larger variety of problems. In addition, generative model estimation enables straightforward inclusion of prior knowledge. The method and apparatus of one embodiment of the present invention using Maximum Entropy Discrimination bridges the gap between pure discriminative, e.g. Support Vector Machine learning, and generative model estimation.

The method of one embodiment of the present invention as shown in Table 3 is an improved transductive MED classification algorithm that does not have the instability problem of the method discussed in Jaakkola, referenced herein. Differences include, but are not limited to, that in one embodiment of the present invention every data point has its own cost factor proportional to its absolute label expectation value |⟨y⟩|. In addition, each data points label prior probability is updated after each M step according to the estimated class membership probability as function of the data point's distance to the decision function. The method of one embodiment of the present invention is described in Table 3 as follows:

Improved Transductive MED Classification
  Require: Data matrix X of labeled and unlabeled training examples
  Require: Label prior probabilities $p_0(y)$ for labeled and unlabeled training examples.
  Require: Global cost factor c.

TABLE 3

1: ⟨Y⟩:=ExpectedLabel($p_o(y)$) {Expected label determined from the training examples' label prior probabilities.}
2: while ¬converged do
3:     C :=|⟨Y⟩|c {Scale each training example's cost factor by the absolute value of its expected label.}
4:     W := MinimizeKLDivergence(X,⟨Y⟩,C)
5:     $p_o(y)$ := EstimateClassProbability(W,⟨Y⟩)
6:     $Y^t$ := InduceLabels(W,X,$p_o(y)$,C)
7:     ⟨Y⟩:=ϵ ⟨Y⟩+ (1−ϵ)$Y^t$
8: end while Scaling the data points cost factors by |⟨y⟩| mitigates the problem that the unlabeled data can have a stronger cumulative pull on the hyperplane than the labeled data, since the cost factors of unlabeled data are now smaller than labeled data cost factors, i.e. each unlabeled data point's individual contribution to the final solution is always smaller than labeled data points individual contribution. However, in case the amount of unlabeled data is much larger then the number of labeled data, the unlabeled data still can influence the final solution more than the labeled data. In addition, the conjunction of cost factor scaling with updating the label prior probability using the estimated class probability solves the problem of the bridge effect outlined above. At the first M steps, unlabeled data have small cost factors yielding an expected label as function of the classification score that is very flat (see FIG. 1) and, accordingly, to some extent all unlabeled data are allowed to pull on the hyperplane, albeit only with small weight. In addition, owing to the updating of the label prior probability, unlabeled data far away from the separating hyperplane do not get assigned an expected label close to zero, but after several iterations a label close to either y=+1 of y=−1 and, thus, are slowly treated like labeled data.

In a specific implementation of the method of one embodiment of the present invention, by assuming a Gaussian prior with zero mean and unit variance for the decision function parameters Θ

$$p_0(\Theta) = \frac{1}{\sqrt{(2\pi)^n}} e^{-\frac{1}{2}\Theta^t\Theta}. \tag{7}$$

The prior distribution over decision function parameters incorporates important prior knowledge of the specific classification problem at hand. Other prior distributions of decision function parameters important for classification problem are for example a multinomial distribution, a Poisson distribution, a Cauchy distribution (Breit-Wigner), a Maxwell-Boltzman distribution or a Bose-Einstein distribution.

The prior distribution over the threshold b of the decision function is given by a Gaussian distribution with mean $\mu_b$ and variance $\sigma_b^2$ $$p_0(b) = \frac{1}{\sqrt{2\pi}\sigma_b} e^{-\frac{1}{2}\frac{(b-\mu_b)^2}{\sigma_b^2}}. \qquad (8)$$

As prior distribution of a data point's classification margin $\gamma_t$ $$p_0(\gamma_t) = ce^{-c(1+\frac{1}{c}-\gamma_t)}, \qquad (9)$$

Was elected, where c is the cost factor. This prior distribution differs from the one used in Jaakkola, referenced herein, which has the form $\exp[-c(1-\gamma)]$. Preferably, the form given in Eq. 9 over the form used in Jaakkola, referenced herein, since it yields a positive expected margin even for cost factor smaller than one, whereas $\exp[-c(1-\gamma)]$ yields a negative expected margin for c<1.

Given these prior distributions, determining the corresponding partition functions Z is straightforward (see for example T. M. Cover and J. A. Thomas, *Elements of Information Theory*, John Wiley & Sons, Inc.) (Cover), and the objective functions $\mathfrak{J} = -\log Z$ are $$\mathfrak{J}_\Theta(\lambda) = -\frac{1}{2}\sum_{t,t'} \langle y_t \rangle \langle y_{t'} \rangle \lambda_t \lambda_{t'} K(X_t, X_{t'}) \qquad (10)$$

$$\mathfrak{J}_b(\lambda) = -\frac{\sigma_b^2}{2}\left(\sum_t \lambda_t \langle y_t \rangle\right)^2 - \mu_b \sum_t \lambda_t \langle y_t \rangle$$

$$\mathfrak{J}_\gamma(\lambda) = \sum_t \left(1 + \frac{1}{c}\right)\lambda_t + \log\left(1 - \frac{\lambda_t}{c}\right).$$

According to Jaakkola, referenced herein the objective function of the M step is $$\mathfrak{J}_\Theta(\lambda) = \mathfrak{J}_\Theta(\lambda) + \mathfrak{J}_b(\lambda) + \mathfrak{J}_\gamma(\lambda) \qquad (11)$$

and the E step's objective function is $$\mathfrak{J}_E(\lambda) = \mathfrak{J}_\gamma(\lambda) - \sum_t \log \sum_{y_t=\pm 1} p_{0,t}(y_t) e^{y_t \lambda_t s_t}, \qquad (12)$$

where $s_t$ is the t-th data point's classification score determined in the previous M step and $p_{0,t}(y_t)$ the data point's binary label prior probability. The label prior is initialized to $p_{0,t}(y_t)=1$ for labeled data and to either the non-informative prior of $p_{0,t}(y_t)=\frac{1}{2}$ or the class prior probability for unlabeled data.

The section herein entitled M STEP describes the algorithm to solve the M step objective function. Also, the section herein entitled E STEP describes the E step algorithm.

The step EstimateClassProbability in line 5 of Table 3 uses the training data to determine the calibration parameters to turn classification scores into class membership probabilities, i.e. the probability of the class given the score p(c|s). Relevant methods for estimating the score calibration to probabilities are described in J. Platt, *Probabilistic outputs for support vector machines and comparison to regularized likelihood methods*, pages 61-74, 2000 (Platt) and B. Zadrozny and C. Elkan, *Transforming classifier scores into accurate multi-class probability estimates*, 2002 (Zadrozny).

Referring particularly to FIG. 3, the cross (x) denotes a labeled negative example, the plus sign (+) a labeled positive example, and the circles (o) unlabeled data. The different plots show separating hyperplanes determined at various iterations of the M step. The 20-th iteration shows the final solution elected by the improved transductive MED classifier. FIG. 3 shows the improved transductive MED classification algorithm applied to the toy dataset introduced above. The parameters used are $c=10, \sigma_b^2=1$, and $\mu_b=0$. Varying c yields separating hyperplanes that are located between $x \approx -0.5$ and $x=0$, whereby with $c<3.5$ the hyperplane is located right to the one unlabeled data with $x<0$ and with $c \geq 3.5$ left to this unlabeled data point.

Figure 4:
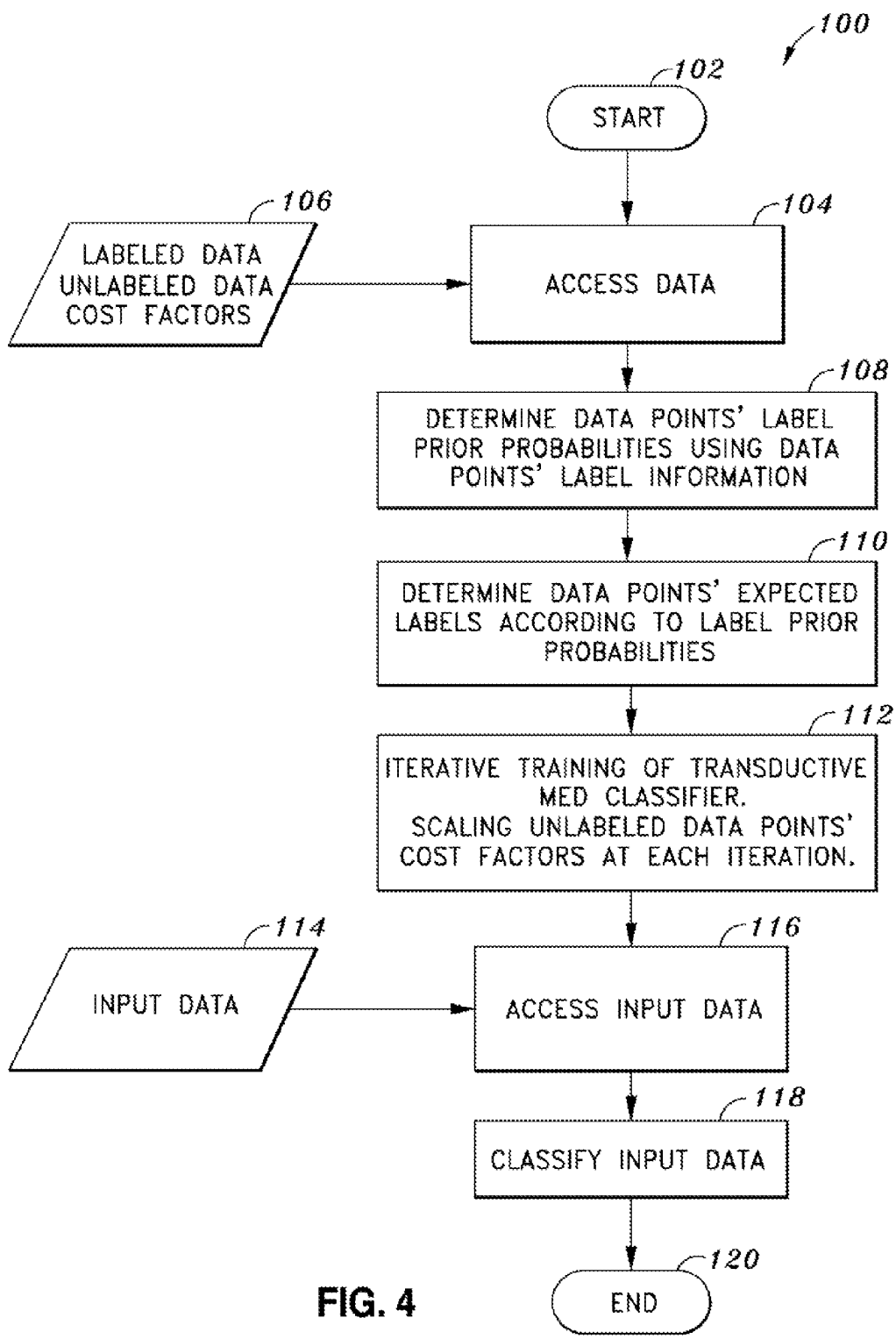
FIG. 4 illustrates a control flow diagram for the classification of unlabeled data in accordance with one embodiment of the invention using a scaled cost factor.

Referring particularly to FIG. 4, a control flow diagram is illustrated showing the method of classification of unlabeled data of one embodiment of the present invention. The method 100 begins at step 102 and at step 104 accesses stored data 106. The data is stored at a memory location and includes labeled data, unlabeled data and at least one predetermined cost factor. The data 106 includes data points having assigned labels. The assigned labels identify whether a labeled data point is intended to be included within a particular category or excluded from a particular category.

Once data is accessed at step 104, the method of one embodiment of the present invention at step 108 then determines the label prior probabilities of the data point using the label information of data point. Then, at step 110 the expected labels of the data point are determined according to the label prior probability. With the expected labels calculated in step 110, along with the labeled data, unlabeled data and cost factors, step 112 includes iterative training of the transductive MED classifier by the scaling of the cost factor unlabeled data points. In each iteration of the calculation the unlabeled data points' cost factors are scaled. As such, the MED classifier learns through repeated iterations of calculations. The trained classifier then accessed input data 114 at step 116. The trained classifier can then complete the step of classifying input data at step 118 and terminates at step 120.

It is to be understood that the unlabeled data of 106 and the input data 114 may be derived from a single source. As such, the input data/unlabeled data can be used in the iterative process of 112 which is then used to classify at 118. Furthermore, one embodiment of the present invention contemplates that the input data 114 maybe include a feedback mechanism to supply the input data to the stored data at 106 such that the MED classifier of 112 can dynamically learn from new data that is input.

Figure 5:
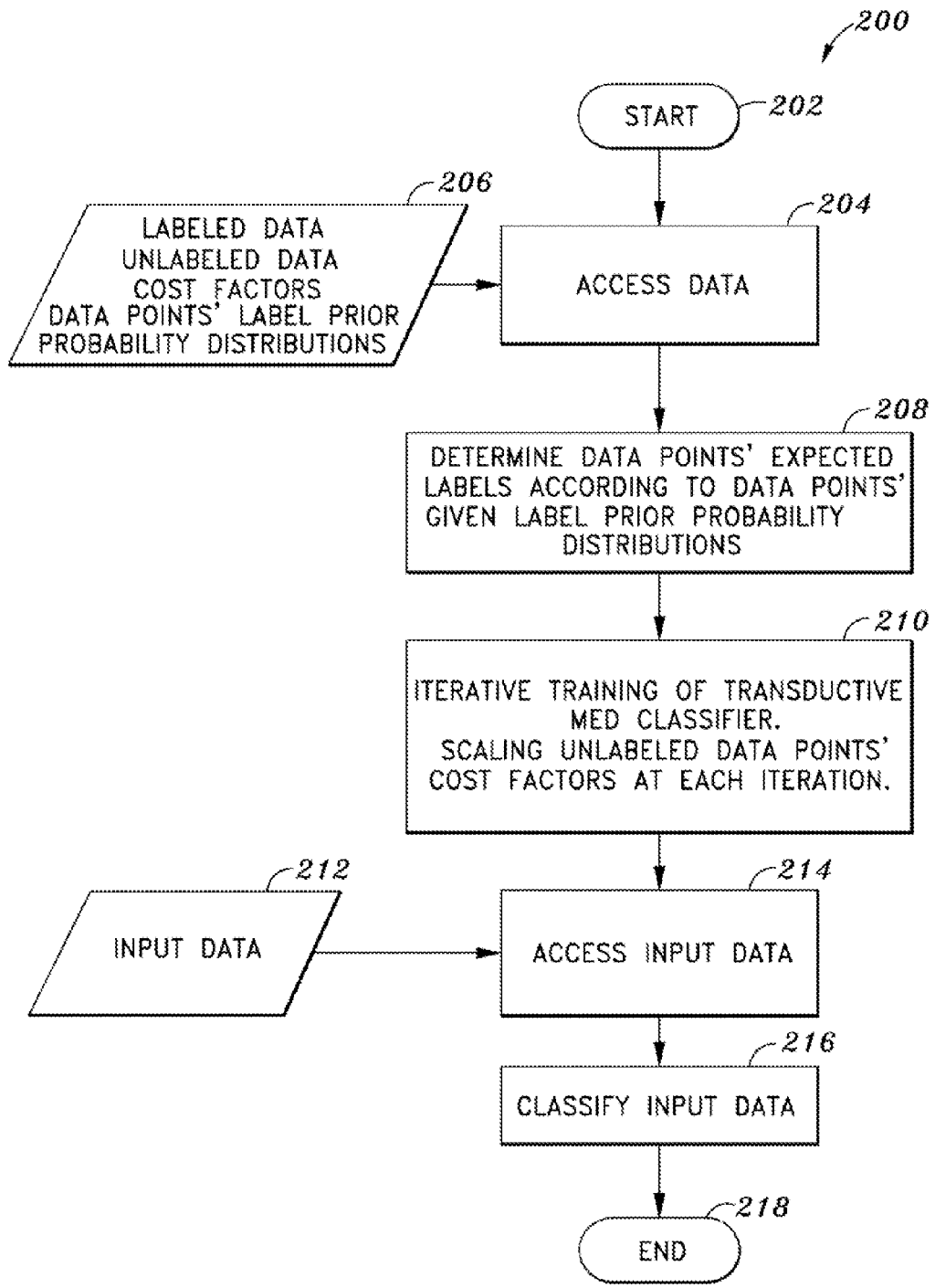
FIG. 5 illustrates a control flow diagram for the classification of unlabeled data in accordance with one embodiment of the invention using user defined prior probability information.

Referring particularly to FIG. 5, a control flow diagram is illustrated showing another method of classification of unlabeled data of one embodiment of the present invention including user defined prior probability information. The method 200 begins at step 202 and at step 204 accesses stored data 206. The data 206 includes labeled data, unlabeled data, a predetermined cost factor, and prior probability information provided by a user. The labeled data of 206 includes data points having assigned labels. The assigned labels identify whether the labeled data point is intended to be included within a particular category or excluded from a particular category.

At step 208, expected labels are calculated from the data of 206. The expected labels then used in step 210 along with labeled data, unlabeled data and cost factors to conduct iterative training of a transductive MED classifier. The iterative calculations of 210 scale the cost factors of the unlabeled data at each calculation. The calculations continue until the classifier is properly trained.

The trained classifier then accessed input data at 214 from input data 212. The trained classifier can then complete the step of classifying input data at step 216. As with the process and method described in FIG. 4, the input data and the unlabeled data may derive from a single source and may be put into the system at both 206 and 212. As such, the input data 212 can influence the training at 210 such that the process my dynamically change over time with continuing input data.

In both methods as shown in FIGS. 4 and 5 a monitor may determine whether or not the system has reached convergence. Convergence may be determined when the change of the hyperplane between each iteration of the MED calculation falls below a predetermined threshold value. In an alternative embodiment of the present invention, the threshold value can be determined when the change of the determined expected label falls below a predetermined threshold value. If convergence is reached, then the iterative training process may cease.

Figure 6:
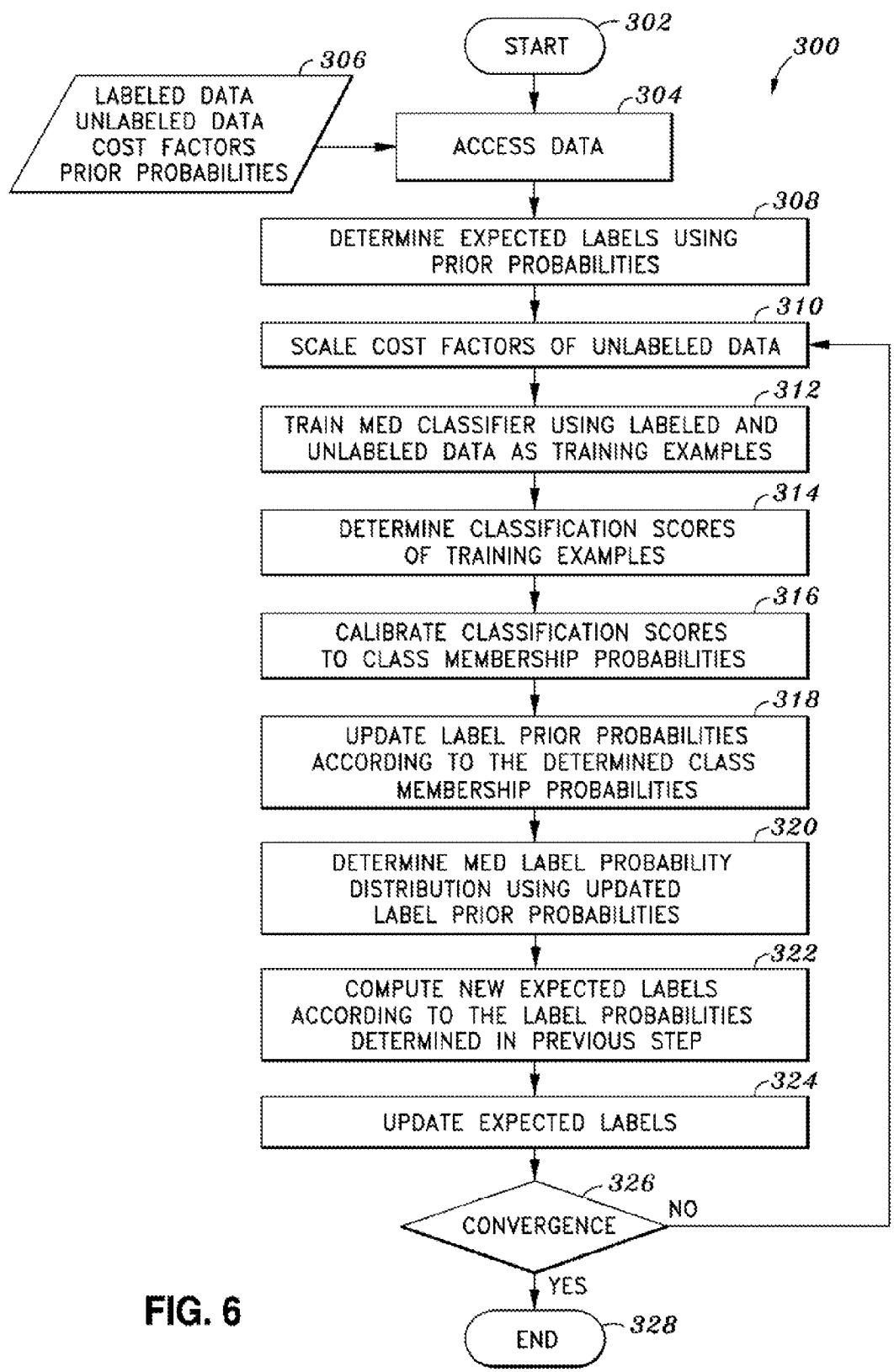
FIG. 6 illustrates a detailed control flow diagram for the classification of unlabeled data in accordance with one embodiment of the invention using Maximum Entropy Discrimination with scaled cost factors and prior probability information.

Referring particularly to FIG. 6, illustrated is a more detailed control flow diagram of the iterative training process of at least one embodiment of the method of the present invention. The process 300 commences at step 302 and at step 304 data is accessed from data 306 and may include labeled data, unlabeled data, at least one predetermined cost factor, and prior probability information. The labeled data points of 306 include a label identifying whether the data point is a training example for data points to be included in the designated category or a training example for data points to be excluded form a designated category. The prior probability information of 306 includes the probability information of labeled data sets and unlabeled data sets.

In step 308, expected labels are determined from the data from the prior probability information of 306. In step 310, the cost factor is scaled for each unlabeled data set proportional to the absolute value of the expected label of a data point. An MED classifier is then trained in step 312 by determining the decision function that maximizes the margin between the included training and excluded training examples utilizing the labeled as well as the unlabeled data as training examples according to their expected labels. In step 314 classification scores are determined using the trained classifier of 312. In 316 classification scores are calibrated to class membership probability. In step 318, label prior probability information is updated according to the class membership probability. An MED calculation is preformed in step 320 to determine label and margin probability distributions, wherein the previously determined classification scores are used in the MED calculation. As a result, new expected labels are computed at step 322 and the expected labels are updated in step 324 using the computations from step 322. At step 326 the method determines whether convergence has been achieved. If so, the method terminates at step 328. If convergence is not reached, another iteration of the method is completed starting with step 310. Iterations are repeated until convergence is reached thus resulting in an iterative training of the MED classifier. Convergence may be reached when change of the decision function between each iteration of the MED calculation falls below a predetermined value. In an alternative embodiment of the present invention, convergence may be reached when the change of the determined expected label value falls below a predetermined threshold value.

Figure 7:
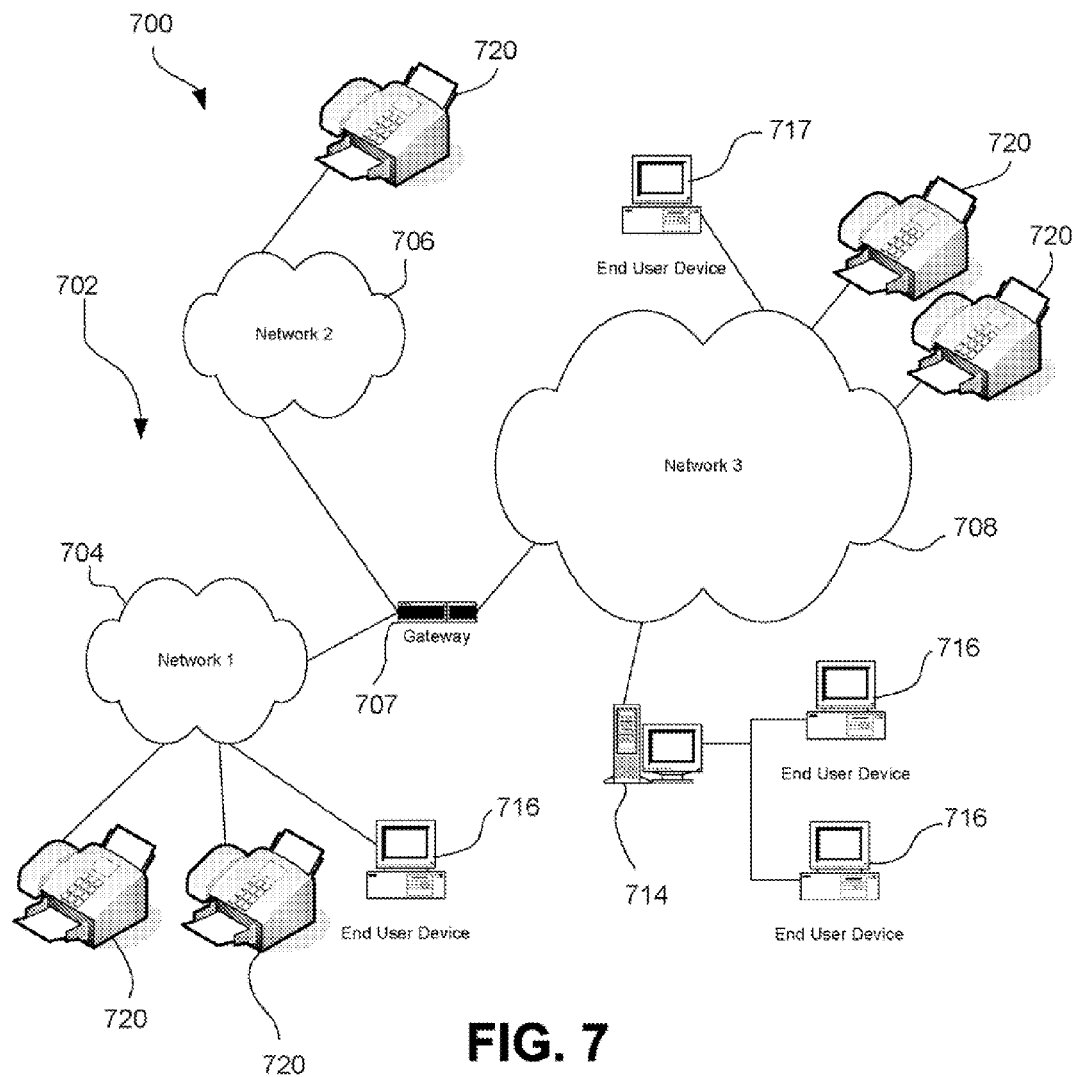
FIG. 7 is a network diagram illustrating a network architecture in which the various embodiments described herein may be implemented.

FIG. 7 illustrates a network architecture 700, in accordance with one embodiment. As shown, a plurality of remote networks 702 are provided including a first remote network 704 and a second remote network 706. A gateway 707 may be coupled between the remote networks 702 and a proximate network 708. In the context of the present network architecture 700, the networks 704, 706 may each take any form including, but not limited to a LAN, a WAN such as the Internet, PSTN, internal telephone network, etc.

In use, the gateway 707 serves as an entrance point from the remote networks 702 to the proximate network 708. As such, the gateway 707 may function as a router, which is capable of directing a given packet of data that arrives at the gateway 707, and a switch, which furnishes the actual path in and out of the gateway 707 for a given packet.

Further included is at least one data server 714 coupled to the proximate network 708, and which is accessible from the remote networks 702 via the gateway 707. It should be noted that the data server(s) 714 may include any type of computing device/groupware. Coupled to each data server 714 is a plurality of user devices 716. Such user devices 716 may include a desktop computer, lap-top computer, hand-held computer, printer or any other type of logic. It should be noted that a user device 717 may also be directly coupled to any of the networks, in one embodiment.

A facsimile machine 720 or series of facsimile machines 720 may be coupled to one or more of the networks 704, 706, 708.

It should be noted that databases and/or additional components may be utilized with, or integrated into, any type of network element coupled to the networks 704, 706, 708. In the context of the present description, a network element may refer to any component of a network.

Figure 8:
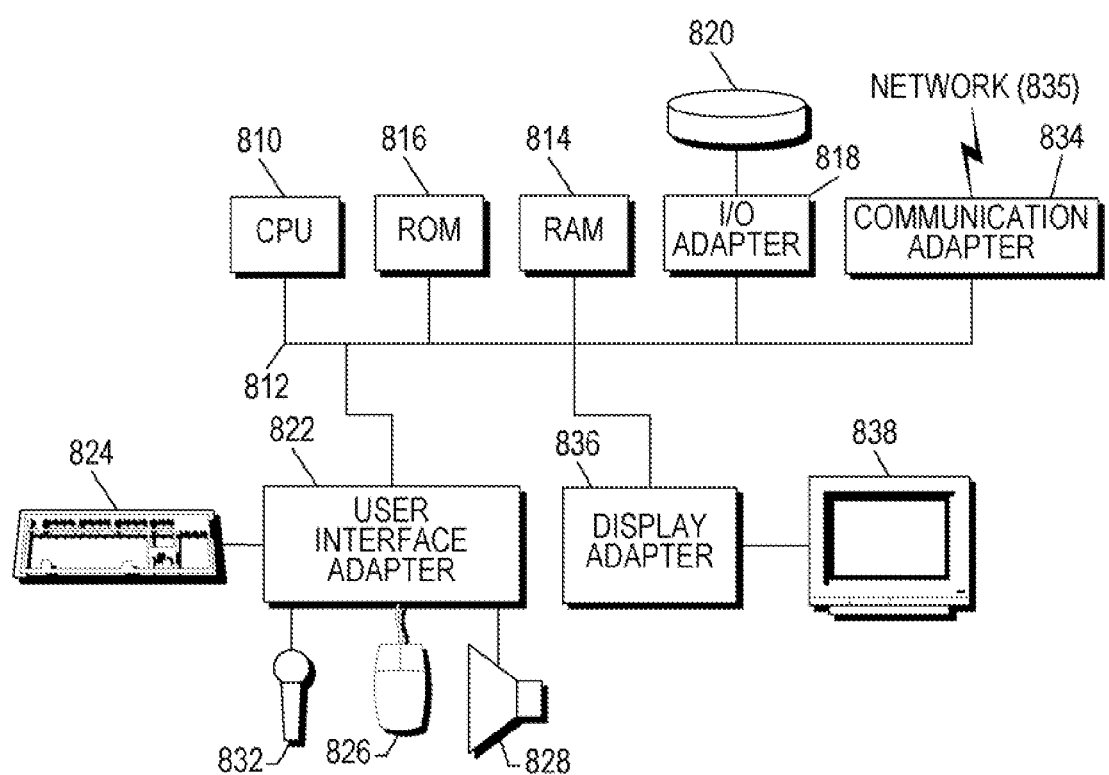
FIG. 8 is a system diagram of a representative hardware environment associated with a user device.

FIG. 8 shows a representative hardware environment associated with a user device 716 of FIG. 7, in accordance with one embodiment. Such Fig. illustrates a typical hardware configuration of a workstation having a central processing unit 810, such as a microprocessor, and a number of other units interconnected via a system bus 812.

The workstation shown in FIG. 8 includes a Random Access Memory (RAM) 814, Read Only Memory (ROM) 816, an I/O adapter 818 for connecting peripheral devices such as disk storage units 820 to the bus 812, a user interface adapter 822 for connecting a keyboard 824, a mouse 826, a speaker 828, a microphone 832, and/or other user interface devices such as a touch screen and a digital camera (not shown) to the bus 812, communication adapter 834 for connecting the workstation to a communication network 835 (e.g., a data processing network) and a display adapter 836 for connecting the bus 812 to a display device 838.

Figure 9:
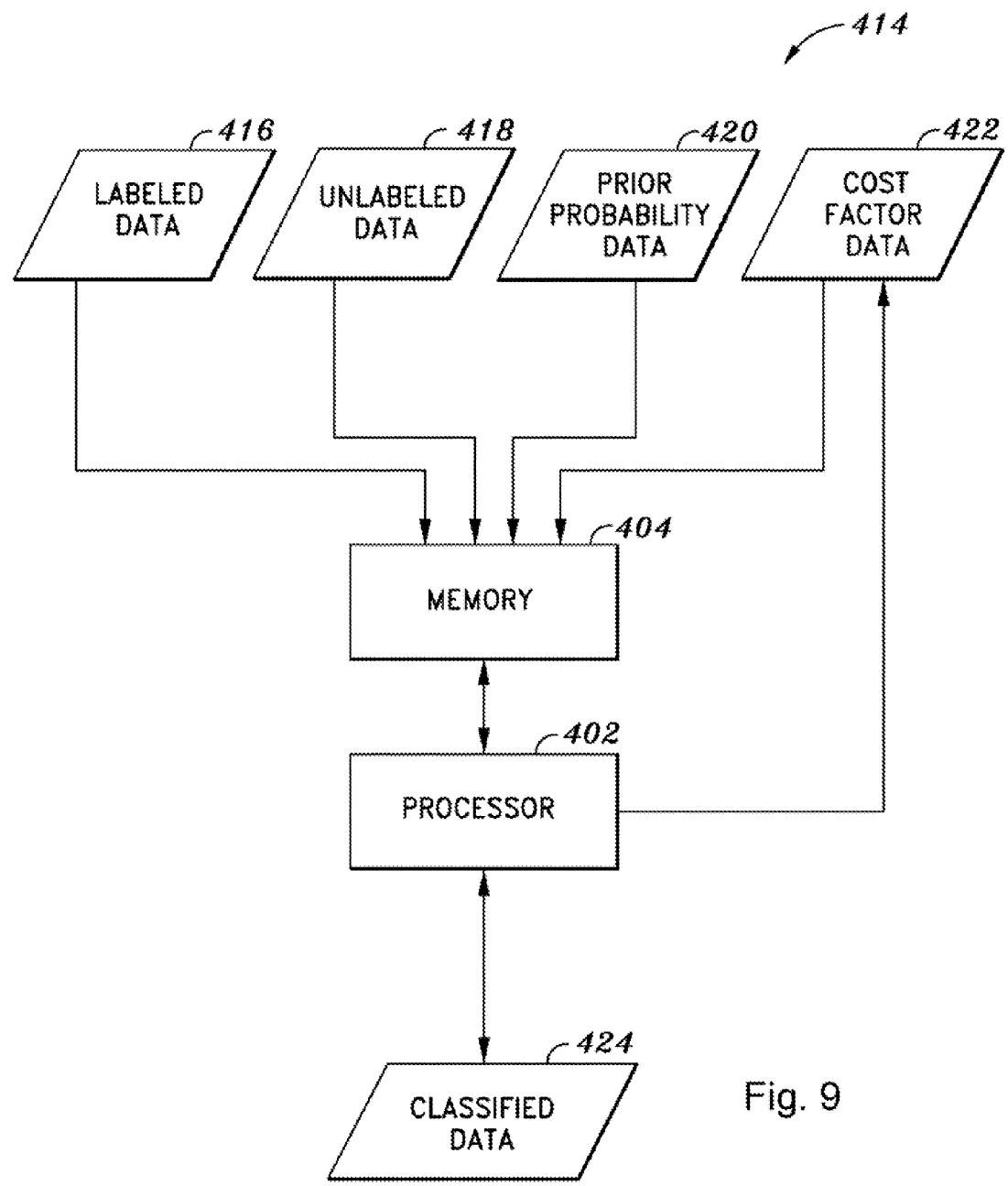
FIG. 9 illustrates a block diagram representation of the apparatus of one embodiment of the present invention.

Referring particularly to FIG. 9 there is shown the apparatus 414 of one embodiment of the present invention. One embodiment of the present invention comprises in memory device 404 for storing labeled data 416. The labeled data points 416 each include a label indicating whether the data point is a training example for data points being included in the designated category or a training example for data points being excluded from a designated category. Memory 404 also stores unlabeled data 418, prior probability data 420 and the cost factor data 422.

The processor 402 accesses the data from the memory 404 and using transductive MED calculations trains a binary classifier enable it to classify unlabeled data. The processor 402 uses iterative transductive calculation by using the cost factor and training examples from labeled and unlabeled data and scaling that cost factor as a function of expected label value thus effecting the data of the cost factor data 422 which is then re-input into processor 402. Thus the cost factor 422 changes with each iteration of the MED classification by the processor 402. Once the processor 402 adequately trains an MED classifier, the processor can then construct the classifier to classify the unlabeled data into classified data 424.

Transductive SVM and MED formulations of the prior art lead to an exponential growth of possible label assignments and approximations have to be developed for practical applications. In an alternative embodiment of the present invention, a different formulation of the transductive MED classification is introduced that does not suffer from an exponential growth of possible label assignments and allows a general closed form solution. For a linear classifier the problem is formulated as follows: Find the distribution over hyperplane parameters $p(\Theta)$, the bias distribution $p(b)$, the data points classification margins $p(\gamma)$ whose combined probability distribution has a minimal Kullback Leibler divergence KL to the combined respective prior distributions $p_0$, i.e.

$$\min_{p(\Theta), p(\gamma), p(b)} = KL(p(\Theta)p(\gamma)p(b)\|p_0(\Theta)p_0(\gamma)p_b(b)), \quad (13)$$

subject to the following constraint for the labeled data $$\forall t: \int d\Theta d\gamma db p(\Theta)p(\gamma)p(b)(y_t(\Theta X_t - b)) - \gamma_t) \geq 0, \quad (14)$$

and subject to the following constraint for the unlabeled data $$\forall t': \int d\Theta d\gamma db p(\Theta)p(\gamma)p(b)((\Theta X_{t'} - b))^2 - \gamma_{t'}) \geq 0, \quad (15)$$

where the $\Theta X_t$ is the dot product between the separating hyperplane's weight vector and the t-th data point's feature vector. No prior distribution over labels is necessary. The labeled data are constrained to be on the right side of the separating hyperplane according to their known labels, whereas the only requirement for the unlabeled data is that their squared distance to the hyperplane is greater than the margin. In summary this embodiment of the present invention finds a separating hyperplane that is a compromise of being closest to the chosen prior distribution, separating the labeled data correctly, and having no unlabeled data between the margins. The advantage is that no prior distribution over labels has to be introduced, thus, avoiding the problem of exponentially growing label assignments.

In specific implementation of the alternate embodiment of the present invention, using the prior distributions given in the Eqs. 7, 8, and 9 for the hyperplane parameters, the bias, and the margins yields the following partition function $$Z(\lambda) = \frac{1}{\sqrt{(2\pi)^{(n+1)}\sigma_b}} \quad (16)$$

$$\int d\Theta db e^{-\frac{1}{2}\Theta^T\Theta - \frac{1}{2}\left(\frac{b-\mu_b}{\sigma_b}\right)^2 + \sum_t \lambda_t y_t(\Theta^T X_t - b) + \sum_{t'} \lambda_{t'}(\Theta^T X_{t'} - b)^2}$$

$$\left(\prod_t \int p_0(\gamma_t)e^{\sum_t \lambda_t \gamma_t} d\gamma_t\right)\left(\prod_{t'} \int p_0(\gamma_{t'})e^{\sum_{t'} \lambda_{t'} \gamma_{t'}} d\gamma_{t'}\right),$$

where subscript t is the index of the labeled data and t' the index of the unlabeled data. Introducing the notation $$Z = \begin{pmatrix} \Theta \\ b - \mu_b \end{pmatrix}, U = \begin{pmatrix} X \\ -1 \end{pmatrix}, \quad (17)$$

-continued $$G_1 = \begin{pmatrix} 1 & 0 & \cdots & 0 \\ 0 & 1 & & \vdots \\ \vdots & & \ddots & \vdots \\ 0 & \cdots & \cdots & \frac{1}{\sigma_b^2} \end{pmatrix},$$

$$G_2 = \sum_{t'} U_{t'}U_{t'}^T, G_3 = G_1 - 2G_2,$$

and $W = \sum_t \lambda_t \gamma_t U_t - 2\sum_{t'} \lambda_{t'} \gamma_{t'} U_{t'},$ Eq. 16 can be rewritten as follows $$Z(\lambda) = \frac{1}{\sqrt{(2\pi)^{n+1}\sigma_b^2}} \quad (18)$$

$$\int dZ e^{-\frac{1}{2}(Z^T G_3 Z - 2Z^T W)} e^{-\mu_b \sum_t y_t \lambda_t + \mu_b^2 \sum_{t'} \lambda_{t'} \Box_\gamma \Box_{\gamma'}},$$

yielding, after integration, the following partition function $$Z(\lambda) = \sqrt{\frac{|G_3^{-1}|}{\sigma_b^2}} e^{+\frac{1}{2}W^T G_3^{-1} W - \mu_b \sum_t y_t \lambda_t + \mu_b^2 \sum_{t'} \lambda_{t'} \Box_\gamma \Box_{\gamma'}}, \quad (19)$$

i.e. the final objective function is $$\mathcal{J}(\lambda) = -\frac{1}{2}\log\frac{|G_3^{-1}|}{\sigma_b^2} - \frac{1}{2}W^T G_3^{-1} W + \mu_b \sum_t y_t \lambda_t + \mu_b^2 \sum_{t'} \lambda_{t'} + \quad (20)$$

$$\sum_t \left(1 + \frac{1}{c}\right)\lambda_t + \log\left(1 - \frac{\lambda_t}{c}\right) + \sum_{t'} \left(1 + \frac{1}{c}\right)\lambda_{t'} + \log\left(1 - \frac{\lambda_{t'}}{c}\right).$$

The objective function $\mathcal{J}$ can be solved by applying similar techniques as in the case of known labels as discussed in the section herein entitled M Step. The difference is that matrix $G_3^{-1}$ in the quadratic form of the maximum margin term has now off-diagonal terms.

There exist many applications of method of the present invention employing Maximum Entropy Discrimination framework besides classification. For example MED can be applied to solve classification of data, in general, any kind of discriminant function and prior distributions, regression and graphical models (T. Jebara, *Machine Learning Discriminative and Generative*, Kluwer Academic Publishers) (Jebara).

The applications of the embodiments of the present invention can be formulated as pure inductive learning problems with known labels as well as a transductive learning problem with labeled as well as unlabeled training examples. In the latter case, the improvements to the transductive MED classification algorithm described in Table 3 are applicable as well to general transductive MED classification, transductive MED regression, transductive MED learning of graphical models. As such, for purposes of this disclosure and the accompanying claims, the word "classification" may include regression or graphical models.

M Step

According to Eq. 11, the M step's objective function is $$\mathcal{J}_M(\lambda) = -\frac{1}{2}\sum_{t,t'} \langle y_t \rangle \langle y_{t'} \rangle \lambda_t \lambda_{t'} K(X_t, X_{t'}) - \frac{\sigma_b^2}{2}\Big(\sum_t \lambda_t \langle y_t \rangle\Big)^2 - \qquad (21)$$
$$\mu_b \sum_t \lambda_t \langle y_t \rangle + \sum_t \Big(1+\frac{1}{c}\Big)\lambda_t + \sum_t \log\Big(1-\frac{\lambda_t}{c}\Big),$$
$$\{\lambda_t \mid 0 \le \lambda_t \le c\},$$

whereby the Lagrange Multipiers $\lambda_t$ are determined by maximizing $J_M$.

Omitting the redundant constraint that $\lambda_t < c$, the Lagrangian for the dual problem above is $$\pounds_M(\lambda) = -\frac{1}{2}\sum_{t,t'} \langle y_t \rangle \langle y_{t'} \rangle \lambda_t \lambda_{t'} K(X_t, X_{t'}) - \frac{\sigma_b^2}{2}\Big(\sum_t \lambda_t \langle y_t \rangle\Big)^2 - \qquad (22)$$
$$\mu_b \sum_t \lambda_t \langle y_t \rangle + \sum_t \Big(1+\frac{1}{c}\Big)\lambda_t + \sum_t \log\Big(1-\frac{\lambda_t}{c}\Big), + \sum_t \delta_t \lambda_t$$
$$\forall t: 0 \le \lambda_t \le c_t \delta_t \ge 0, \delta_t \lambda_t = 0.$$

The KKT conditions, which are necessary and sufficient for optimality, are $$\frac{d\pounds_M(\lambda)}{d\lambda} = -\sum_{t'} \langle y_t \rangle \langle y_{t'} \rangle \lambda_{t'} K(X_t, X_{t'}) - \sigma_b^2 \langle y_t \rangle \sum_{t'} \lambda_{t'} \langle y_{t'} \rangle - \qquad (23)$$
$$\mu_b \langle y_t \rangle + \Big(1+\frac{1}{c}\Big) - \frac{1}{c-\lambda_t} + \delta_t$$
$$= -\sum_{t'} \langle y_t \rangle \langle y_{t'} \rangle \lambda_{t'} K(X_t, X_{t'}) - \sigma_b^2 \langle y_t \rangle \sum_{t'} \lambda_{t'} \langle y_{t'} \rangle -$$
$$\mu_b \langle y_t \rangle + \frac{\langle y_t \rangle}{\langle y_t \rangle}\Big(1+\frac{1}{c}\Big) - \frac{\langle y_t \rangle}{\langle y_t \rangle (c-\lambda_t)} + \delta_t$$
$$= \langle y_t \rangle \begin{pmatrix} -\sum_{t'} \langle y_{t'} \rangle \lambda_{t'} K(X_t, X_{t'}) - \\ \sigma_b^2 \sum_{t'} \lambda_{t'} \langle y_{t'} \rangle - \mu_b + \\ \frac{1}{\langle y_t \rangle}\Big(1+\frac{1}{c}\Big) - \frac{1}{\langle y_t \rangle(c-\lambda_t)} \end{pmatrix} + \delta_t$$
$$= \langle y_t \rangle \Big(-F_t - \sigma_b^2 \sum_{t'} \lambda_{t'} \langle y_{t'} \rangle - \mu_b\Big) + \delta_t$$
$$= 0$$
$$\forall t: 0\delta_t \ge 0, \delta_t \lambda_t = 0$$

whereby $F_t$ is $$F_t = \sum_{t'} \langle y_{t'} \rangle \lambda_{t'} K(X_t, X_{t'}) + \frac{1}{\langle y_t \rangle}\Big(1+\frac{1}{c}\Big) - \frac{1}{\langle y_t \rangle(c-\lambda_t)}. \qquad (24)$$

At optimum, the basis equals the expected bias $\langle b \rangle = \sigma_b^2 \Sigma_t \lambda_t \langle y_t \rangle + \mu_b$ yielding $$\langle y_t \rangle (-F_t - \langle b \rangle) + \delta_t = 0 \qquad (25)$$

These equations can be summarized by considering two cases using the $\delta_t \lambda_t = 0$ constraint. The first case for all $\lambda_t = 0$, and second for all $0 < \lambda_t < c$. There is no need for the third case as described in S. Keerthi, S. Shevade, C. Bhattacharyya, and K. Murthy, *Improvements to platt's smo algorithm for svm classifier design*, 1999 (Keerthi), applied to the SVM algorithm; the potential function in this formulation maintains that $\lambda_t \ne c$.

$$\lambda_{tb=0,\delta_t} \ge 0 \Rightarrow (F_t + \langle b \rangle)\langle y_t \rangle \ge 0 \qquad (26)$$

$$0 < \lambda_t < c, \delta_t = 0 \Rightarrow (F_t + \langle b \rangle) = 0 \qquad (27)$$

Until the optimum is reached, violations of these conditions for some data point t will be present. Namely, $F_t \ne -\langle b \rangle$ when $\lambda_t$ is nonzero or $F_t \langle y_t \rangle < -\langle b \rangle \langle y_t \rangle$ when it is zero. Unfortunately, calculating $\langle b \rangle$ is impossible without the optimum $\lambda_t$'s. A good solution to this is borrowed from Keerthi, referenced herein again, by constructing the following three sets.

$$I_0 = \{t : 0 < \lambda_t < c\} \qquad (28)$$

$$I_1 = \{t : \langle y_t \rangle > 0, \lambda_t = 0\} \qquad (29)$$

$$I_4 = \{t : \langle y_t \rangle < 0, \lambda_t = 0\} \qquad (30)$$

Using these sets we can define the most extreme violations of the optimality conditions using the following definitions. The elements in $I_0$ are violations whenever they are not equal to $-\langle b \rangle$, therefore, the largest and smallest $F_t$ from $I_0$ are candidates for being violations. The elements in $I_1$ are violations when $F_t < -\langle b \rangle$ so the smallest element from $I_1$ is the most extreme violation if one exists. Lastly, the elements in $I_4$ are violations when $F_t > -\langle b \rangle$, which makes the lamest elements from $I_4$ violation candidates. Therefore, $-\langle b \rangle$ is bounded by the min and max over these sets as shown below.

$$-b_{up} = F_t^{min}\{F_t : t \in I_0 \cup I_1\} \qquad (31)$$

$$-b_{low} = F_t^{max}\{F_t : t \in I_0 \cup I_4\} \qquad (32)$$

Due to the fact that at optimum $-b_{up}$ and $-b_{low}$ must be equal, namely $-\langle b \rangle$, then reducing the gap between $-b_{up}$ and $-b_{low}$ will push the training algorithm to convergence. Additionally, the gap can also be measured as a way to determine numerical convergence.

As previously stated, the value of $b = \langle b \rangle$ is not known until convergence. The method of this alternate embodiment differs in that only one example can be optimized at a time. Therefore the training heuristic is to alternate between the examples in $I_0$ and all of the examples every other time.

E Step

The E step's objective function of Eq. 12 is $$\mathcal{J}_E(\lambda) = \sum_t \Big(1+\frac{1}{c}\Big)\lambda_t + \log\Big(1-\frac{\lambda_t}{c}\Big) - \qquad (33)$$
$$\sum_t \log \sum_{y_t = \pm 1} p_{0,t}(y_t) e^{y_t \lambda_t s_t} \{\lambda_t \mid 0 \le \lambda_t \le c\},$$

whereby $s_t$ is the t-th datapoint's classification score determined in the previous M step. The Lagrange Multipliers $\lambda_t$ are determined by maximizing $\mathcal{J}_E$.

Omitting the redundant constraint that $\lambda_t < c$, the Lagrangian for the dual problem above is:

$$\pounds_E(\lambda) = \sum_t \Big(1+\frac{1}{c}\Big)\lambda_t + \log\Big(1-\frac{\lambda_t}{c}\Big) - \qquad (34)$$
$$\sum_t \log \sum_{y_t = \pm 1} p_{0,t}(y_t) e^{y_t \lambda_t s_t} + \sum_t \delta_t \lambda_t,$$
$$\forall t: 0 \le \lambda_t \le c, \delta_t \ge 0, \delta_t \lambda_t = 0$$

The KKT conditions, which are necessary and sufficient for optimality, are $$\frac{\partial L(\lambda)}{\partial \lambda_t} = \left(1 - \frac{1}{c}\right) - \frac{1}{c - \lambda_t} - \quad (35)$$
$$s_t \frac{P_{0,t}(+1)e^{\lambda_t s_t} - P_{0,t}(-1)e^{-\lambda_t s_t}}{P_{0,t}(+1)e^{\lambda_t s_t} + P_{0,t}(-1)e^{-\lambda_t s_t}} + \delta_t$$
$$= 0.$$

Solving for the Lagrange5 multipliers by optimizing the KKT conditions can be done in one pass over the exampled since they factorize over the examples.

For labeled examples the expected label $\langle y_t \rangle$ is one with $P_{0,t}(y_t)=1$ and $P_{0,t}(-y_t)=0$ reducing the KKT conditions to $$\frac{\partial L_E(\lambda)}{\partial \lambda_t} = \left(1 - \frac{1}{c}\right) - \frac{1}{c - \lambda_t} - s_t \langle y_t \rangle + \delta_t = 0 \quad (36)$$

and yielding as solutions for the Lagrange Multipliers of labeled examples $$\lambda_t = \frac{c - 1 - c \langle y_t \rangle s_t}{\left(1 - \frac{1}{c}\right) \langle y_t \rangle s_t}. \quad (37)$$

For unlabeled examples, Eq. 35 cannot be solved analytically, but has to be determined by applying e.g. a linear search for each unlabeled example's Lagrange Multiplier that satisfies Eq. 35.

The following are several non-limiting examples that are enabled by the techniques illustrated above, derivations or variations thereof and other techniques known in the art. Each example includes the preferred operations, along with optional operations or parameters that may be implemented in the basic preferred methodology.

Figure 10:
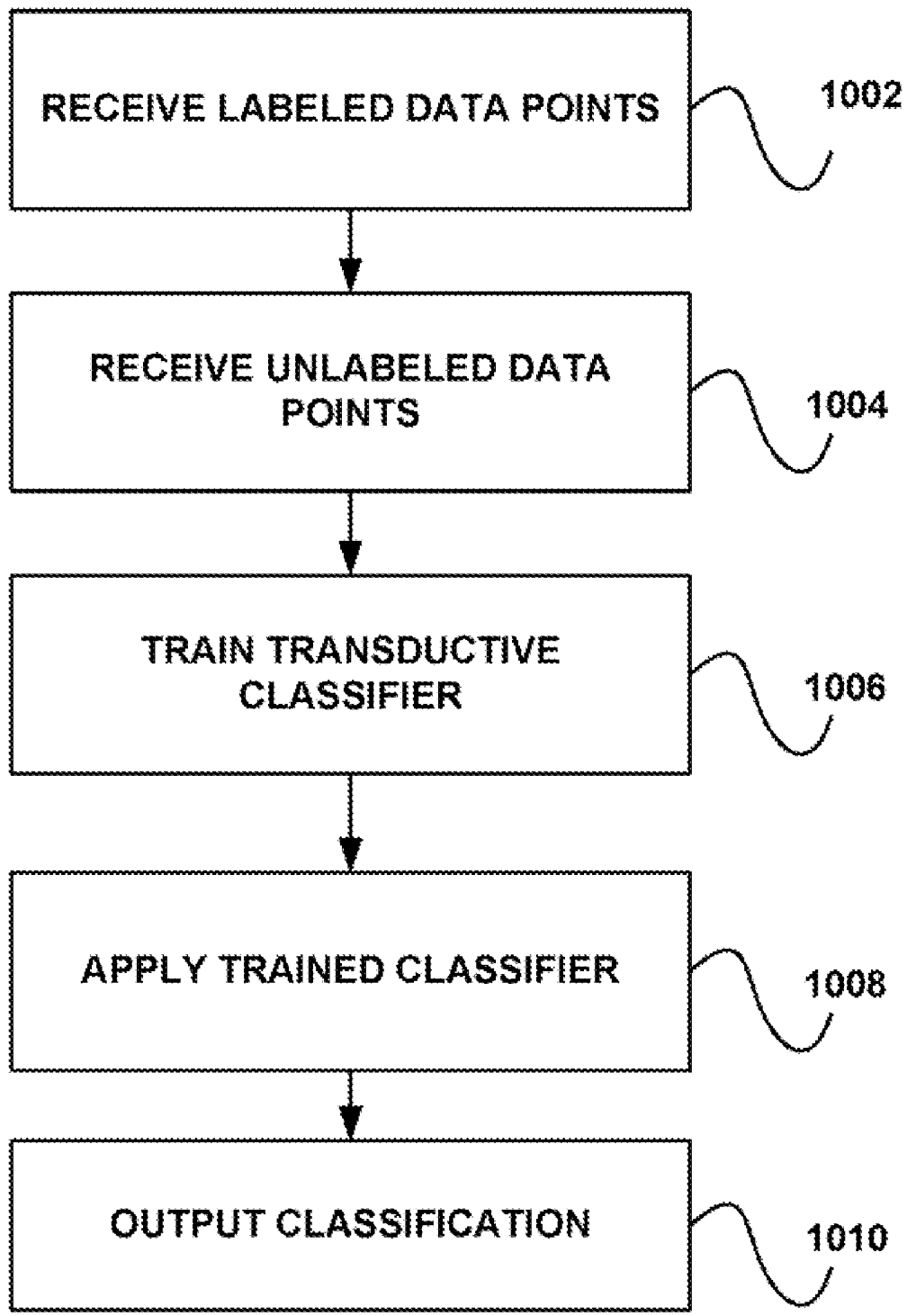
FIG. 10 illustrates, in a flowchart, a classification process performed by in accordance with one embodiment.

In one embodiment, as presented in FIG. 10, labeled data points are received at step 1002, where each of the labeled data points has at least one label which indicates whether the data point is a training example for data points for being included in a designated category or a training example for data points being excluded from a designated category. In addition, unlabeled data points are received at step 1004, as well as at least one predetermined cost factor of the labeled data points and unlabeled data points. The data points may contain any medium, e.g. words, images, sounds, etc. Prior probability information of labeled and unlabeled data points may also be received. Also, the label of the included training example may be mapped to a first numeric value, e.g. +1, etc., and the label of the excluded training example may be mapped to a second numeric value, e.g. −1, etc. In addition, the labeled data points, unlabeled data points, input data points, and at least one predetermined cost factor of the labeled data points and unlabeled data points may be stored in a memory of a computer.

Further, at step 1006 a transductive MED classifier is trained through iterative calculation using said at least one cost factor and the labeled data points and the unlabeled data points as training examples. For each iteration of the calculations, the unlabeled data point cost factor is adjusted as a function of an expected label value, e.g. the absolute value of the expected label of a data point, etc., and a data point label prior probability is adjusted according to an estimate of a data point class membership probability, thereby ensuring stability. Also, the transductive classifier may learn using prior probability information of the labeled and unlabeled data, which further improves stability. The iterative step of training a transductive classifier may be repeated until the convergence of data values is reached, e.g. when the change of the decision function of the transductive classifier falls below a predetermined threshold value, when the change of the determined expected label value falls below a predetermined threshold value, etc.

Additionally, in step 1008 the trained classifier is applied to classify at least one of the unlabeled data points, the labeled data points, and input data points. Input data points may be received before or after the classifier is trained, or may not be received at all. Also, the decision function that minimizes the KL divergence to the prior probability distribution of the decision function parameters given the included and excluded training examples may be determined utilizing the labeled as well as the unlabeled data points as learning examples according to their expected label. Alternatively, the decision function may be determined with minimal KL divergence using a multinomial distribution for the decision function parameters.

In step 1010 a classification of the classified data points, or a derivative thereof, is output to at least one of a user, another system, and another process. The system may be remote or local. Examples of the derivative of the classification may be, but are not limited to, the classified data points themselves, a representation or identifier of the classified data points or host file/document, etc.

In another embodiment, computer executable program code is deployed to and executed on a computer system. This program code comprises instructions for accessing stored labeled data points in a memory of a computer, where each of said labeled data points has at least one label indicating whether the data point is a training example for data points for being included in a designated category or a training example for data points being excluded from a designated category. In addition, the computer code comprises instructions for accessing unlabeled data points from a memory of a computer as well as accessing at least one predetermined cost factor of the labeled data points and unlabeled data points from a memory of a computer. Prior probability information of labeled and unlabeled data points stored in a memory of a computer may also be accessed. Also, the label of the included training example may be mapped to a first numeric value, e.g. +1, etc., and the label of the excluded training example may be mapped to a second numeric value, e.g. −1, etc.

Further, the program code comprises instructions for training a transductive classifier through iterative calculation, using the at least one stored cost factor and stored labeled data points and stored unlabeled data points as training examples. Also, for each iteration of the calculation, the unlabeled data point cost factor is adjusted as a function of the expected label value of the data point, e.g. the absolute value of the expected label of a data point. Also, for each iteration, the prior probability information may be adjusted according to an estimate of a data point class membership probability. The iterative step of training a transductive classifier may be repeated until the convergence of data values is reached, e.g. when the change of the decision function of the transductive classifier falls below a predetermined threshold value, when the change of the determined expected label value falls below a predetermined threshold value, etc.

Additionally, the program code comprises instructions for applying the trained classifier to classify at least one of the unlabeled data points, the labeled data points, and input data points, as well as instructions for outputting a classification of the classified data points, or derivative thereof, to at least one of a user, another system, and another process. Also, the decision function that minimizes the KL divergence to the prior probability distribution of the decision function parameters given the included and excluded training examples may be determined utilizing the labeled as well as the unlabeled data as learning examples according to their expected label.

In yet another embodiment, a data processing apparatus comprises at least one memory for storing: (i) labeled data points, wherein each of said labeled data points have at least one label indicating whether the data point is a training example for data points being included in a designated category or a training example for data points being excluded from a designated category; (ii) unlabeled data points; and (iii) at least one predetermined cost factor of the labeled data points and unlabeled data points. The memory may also store prior probability information of labeled and unlabeled data points. Also, the label of the included training example may be mapped to a first numeric value, e.g. +1, etc., and the label of the excluded training example may be mapped to a second numeric value, e.g. −1, etc.

In addition, the data processing apparatus comprises a transductive classifier trainer to iteratively teach the transductive classifier using transductive Maximum Entropy Discrimination (MED) using the at least one stored cost factor and stored labeled data points and stored unlabeled data points as training examples. Further, at each iteration of the MED calculation the cost factor of the unlabeled data point is adjusted as a function of the expected label value of the data point, e.g. the absolute value of the expected label of a data point, etc. Also, at each iteration of the MED calculation, the prior probability information may be adjusted according to an estimate of a data point class membership probability. The apparatus may further comprise a means for determining the convergence of data values, e.g. when the change of the decision function of the transductive classifier calculation falls below a predetermined threshold value, when the change of the determined expected label values falls below a predetermined threshold value, etc., and terminating calculations upon determination of convergence.

In addition, a trained classifier is used to classify at least one of the unlabeled data points, the labeled data points, and input data points. Further, the decision function that minimizes the KL divergence to the prior probability distribution of the decision function parameters given the included and excluded training examples may be determined by a processor utilizing the labeled as well as the unlabeled data as learning examples according to their expected label. Also, a classification of the classified data points, or derivative thereof, is output to at least one of a user, another system, and another process.

In a further embodiment, an article of manufacture comprises a program storage medium readable by a computer, where the medium tangibly embodies one or more programs of instructions executable by a computer to perform a method of data classification. In use, labeled data points are received, where each of the labeled data points has at least one label which indicates whether the data point is a training example for data points for being included in a designated category or a training example for data points being excluded from a designated category. In addition, unlabeled data points are received, as well as at least one predetermined cost factor of the labeled data points and unlabeled data points. Prior probability information of labeled and unlabeled data points may also be stored in a memory of a computer. Also, the label of the included training example may be mapped to a first numeric value, e.g. +1, etc., and the label of the excluded training example may be mapped to a second numeric value, e.g. −1, etc.

Further, a transductive classifier is trained with iterative Maximum Entropy Discrimination (MED) calculation using the at least one stored cost factor and the stored labeled data points and the unlabeled data points as training examples. At each iteration of the MED calculation, the unlabeled data point cost factor is adjusted as a function of an expected label value of the data point, e.g. the absolute value of the expected label of a data point, etc. Also, at each iteration of the MED calculation, the prior probability information may be adjusted according to an estimate of a data point class membership probability. The iterative step of training a transductive classifier may be repeated until the convergence of data values is reached, e.g. when the change of the decision function of the transductive classifier falls below a predetermined threshold value, when the change of the determined expected label value falls below a predetermined threshold value, etc.

Additionally, input data points are accessed from the memory of a computer, and the trained classifier is applied to classify at least one of the unlabeled data points, the labeled data points, and input data points. Also, the decision function that minimizes the KL divergence to the prior probability distribution of the decision function parameters given the included and excluded training examples may be determined utilizing the labeled as well as the unlabeled data as learning examples according to their expected label. Further, a classification of the classified data points, or a derivative thereof, is output to at least one of a user, another system, and another process.

In yet another embodiment, a method for classification of unlabeled data in a computer-based system is presented. In use, labeled data points are received, each of said labeled data points having at least one label indicating whether the data point is a training example for data points for being included in a designated category or a training example for data points being excluded from a designated category.

Additionally, labeled and unlabeled data points are received, as are prior label probability information of labeled data points and unlabeled data points. Further, at least one predetermined cost factor of the labeled data points and unlabeled data points is received.

Further, the expected labels for each labeled and unlabeled data point are determined according to the label prior probability of the data point. The following substeps are repeated until substantial convergence of data values:

generating a scaled cost value for each unlabeled data point proportional to the absolute value of the data point's expected label;

training a Maximum Entropy Discrimination (MED) classifier by determining the decision function that minimizes the KL divergence to the prior probability distribution of the decision function parameters given the included training and excluded training examples utilizing the labeled as well as the unlabeled data as training examples according to their expected label;

determining the classification scores of the labeled and unlabeled data points using the trained classifier;

calibrating the output of the trained classifier to class membership probability;

updating the label prior probabilities of the unlabeled data points according to the determined class membership probabilities;

determining the label and margin probability distributions using Maximum Entropy Discrimination (MED) using the updated label prior probabilities and the previously determined classification scores;

computing new expected labels using the previously determined label probability distribution; and updating expected labels for each data point by interpolating the new expected labels with the expected label of previous iteration.

Also, a classification of the input data points, or derivative thereof, is output to at least one of a user, another system, and another process.

Convergence may be reached when the change of the decision function falls below a predetermined threshold value. Additionally, convergence may also be reached when the change of the determined expected label value falls below a predetermined threshold value. Further, the label of the included training example may have any value, for example, a value of +1, and the label of the excluded training example may have any value, for example, a value of −1.

Figure 11:
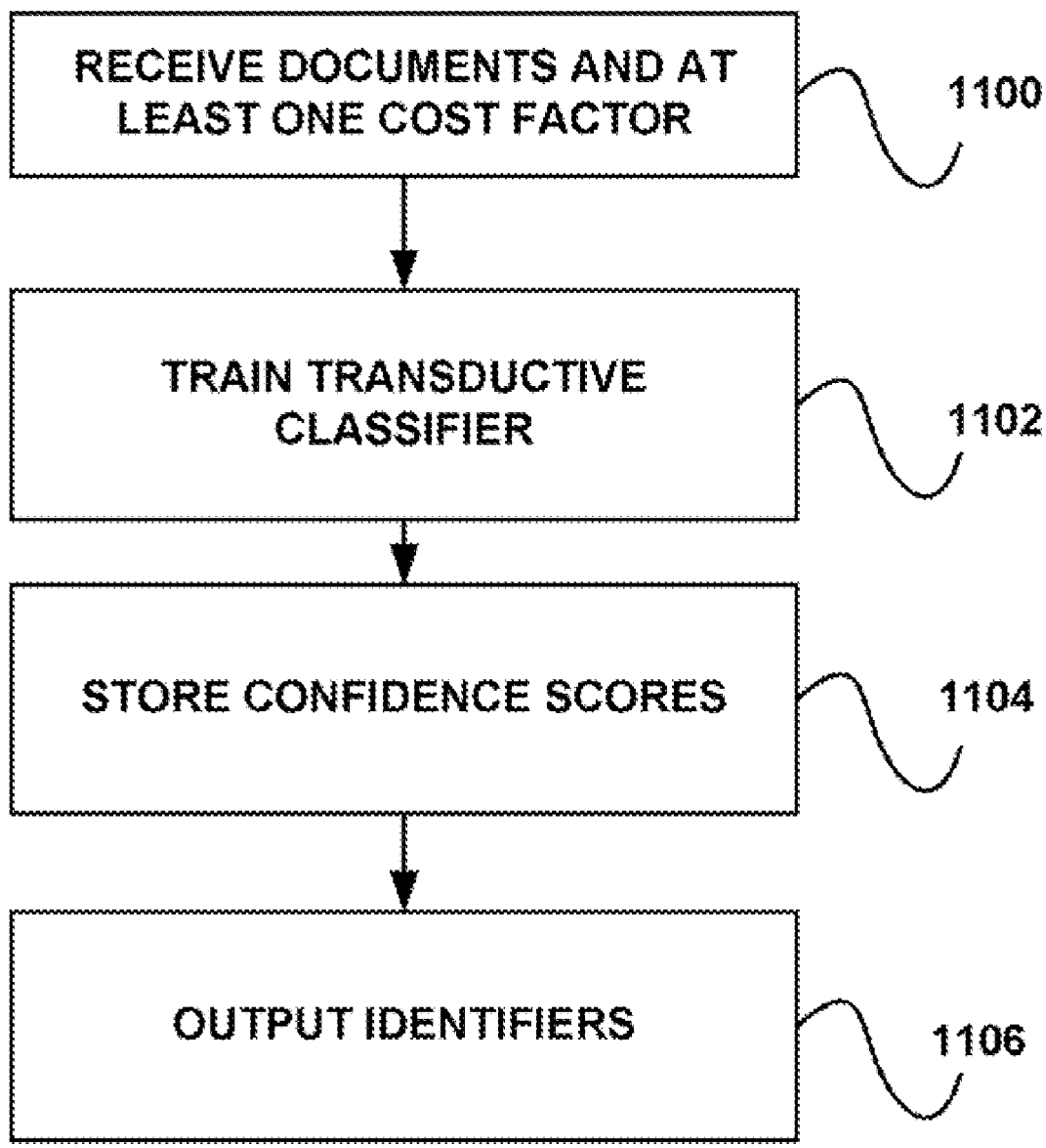
FIG. 11 illustrates, in a flowchart, a classification process performed by in accordance with one embodiment.

In one embodiment of the present invention, a method for classifying documents is presented in FIG. 11. In use, at least one seed document having a known confidence level is received in step 1100, as well as unlabeled documents and at least one predetermined cost factor. The seed document and other items may be received from a memory of a computer, from a user, from a network connection, etc., and may be received after a request from the system performing the method. The at least one seed document may have a label indicative of whether the document is included in a designated category, may contain a list of keywords, or have any other attribute that may assist in classifying documents. Further, in step 1102 a transductive classifier is trained through iterative calculation using the at least one predetermined cost factor, the at least one seed document, and the unlabeled documents, wherein for each iteration of the calculations the cost factor is adjusted as a function of an expected label value. A data point label prior probability for the labeled and unlabeled documents may also be received, wherein for each iteration of the calculations the data point label prior probability may be adjusted according to an estimate of a data point class membership probability.

Additionally, after at least some of the iterations, in step 1104 confidence scores are stored for the unlabeled documents, and identifiers of the unlabeled documents having the highest confidence scores are output in step 1106 to at least one of a user, another system, and another process. The identifiers may be electronic copies of the document themselves, portions thereof, titles thereof, names thereof, file names thereof, pointers to the documents, etc. Also, confidence scores may be stored after each of the iterations, wherein an identifier of the unlabeled document having the highest confidence score after each iteration is output.

One embodiment of the present invention is capable of discovering patterns that link the initial document to the remaining documents. The task of discovery is one area where this pattern discovery proves particularly valuable. For instance, in pre-trial legal discovery, a large amount of documents have to be researched with regard to possible connections to the lawsuit at hand. The ultimate goal is to find the "smoking gun." In another example, a common task for inventors, patent examiners, as well as patent lawyers is to evaluate the novelty of a technology through prior art search. In particular the task is to search all published patents and other publications and find documents within this set that might be related to the specific technology that is examined with regard to its novelty.

The task of discovery involves finding a document or a set of documents within a set of data. Given an initial document or concept, a user may want to discover documents that are related to the initial document or concept. However, the notion of relationship between the initial document or concept and the target documents, i.e. the documents that are to be discovered, is only well understood after the discovery has taken place. By learning from labeled and unlabeled documents, concepts, etc., the present invention can learn patterns and relationships between the initial document or documents and the target documents.

Figure 12:
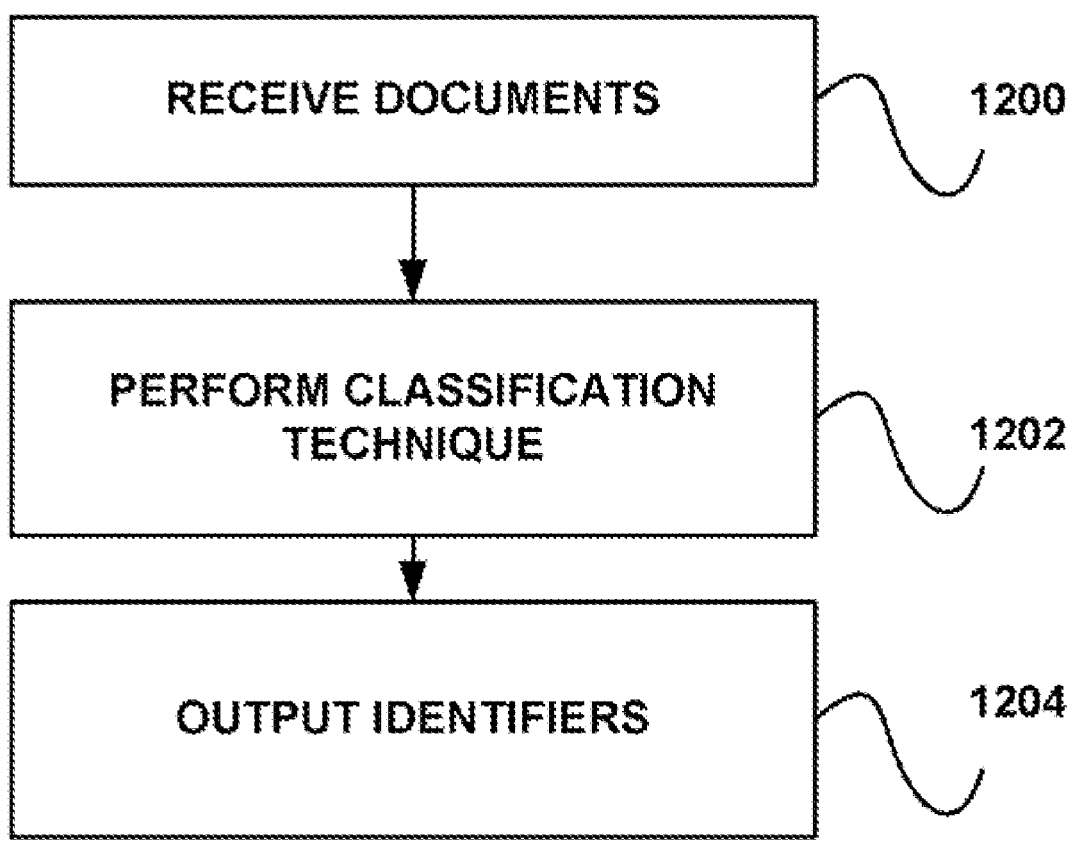
FIG. 12 illustrates, in a flowchart, a classification process performed by in accordance with one embodiment.

In another embodiment of the present invention, a method for analyzing documents associated with legal discovery is presented in FIG. 12. In use, documents associated with a legal matter are received in step 1200. Such documents may include electronic copies of the document themselves, portions thereof titles thereof, names thereof, file names thereof, pointers to the documents, etc. Additionally, a document classification technique is performed on the documents in step 1202. Further, identifiers of at least some of the documents are output in step 1204 based on the classification thereof. As an option, a representation of links between the documents may also be output The document classification technique may include any type of process, e.g. a transductive process, etc. For example, any inductive or transductive technique described above may be used. In a preferred approach, a transductive classifier is trained through iterative calculation using at least one predetermined cost factor, at least one seed document, and the documents associated with the legal matter. For each iteration of the calculations the cost factor is preferably adjusted as a function of an expected label value, and the trained classifier is used to classify the received documents. This process may further comprise receiving a data point label prior probability for the labeled and unlabeled documents, wherein for each iteration of the calculations the data point label prior probability is adjusted according to an estimate of a data point class membership probability. Additionally, the document classification technique may include one or more of a support vector machine process and a maximum entropy discrimination process.

Figure 13:
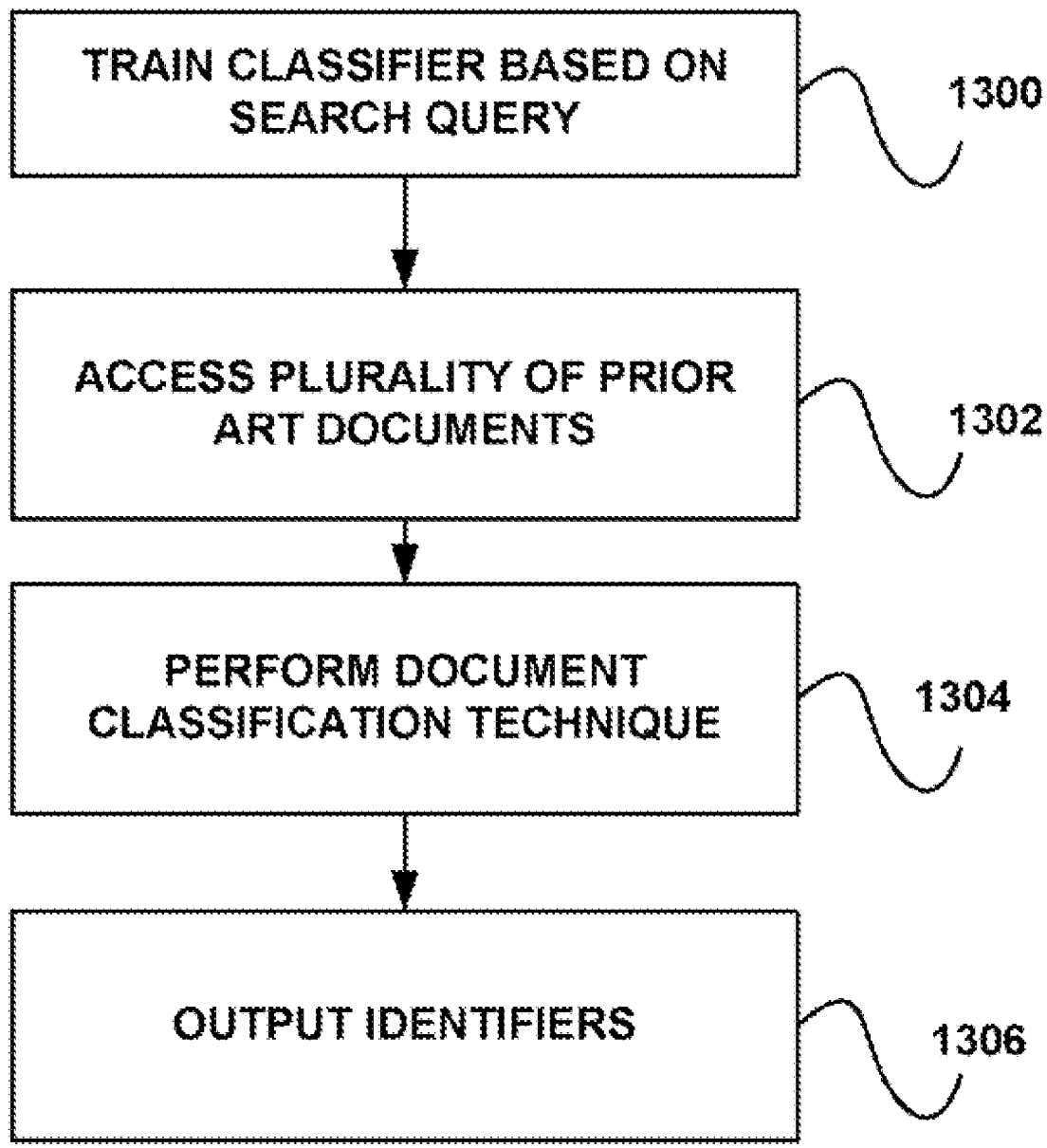
FIG. 13 illustrates, in a flowchart, a classification process performed by in accordance with one embodiment.

In yet another embodiment, a method for analyzing prior art documents is presented in FIG. 13. In use, a classifier is trained based on a search query in step 1300. A plurality of prior art documents are accessed in step 1302. Such prior art may include any information that has been made available to the public, in any form before a given date. Such prior art may also or alternatively include any information that has not been made available to the public in any form before a given date. Illustrative prior art documents may be any type of documents, e.g. publications of a patent office, data retrieved from a database, a collection of prior art, portions of a website, etc. Also, a document classification technique is performed on at least some of the prior art documents in step 1304 using the classifier, and identifiers of at least some of the prior art documents are output in step 1306 based on the classification thereof. The document classification technique may include one or more of any process, including a support vector machine process, a maximum entropy discrimination process, or any inductive or transductive technique described above. Also or alternatively, a representation of links between the documents may also be output. In yet another embodiment, a relevance score of at least some of the prior art documents is output based on the classification thereof.

The search query may include at least a portion of a patent disclosure. Illustrative patent disclosures include a disclosure created by an inventor summarizing the invention, a provisional patent application, a nonprovisional patent application, a foreign patent or patent application, etc.

In one preferred approach, the search query includes at least a portion of a claim from a patent or patent application. In another approach, the search query includes at least a portion of an abstract of a patent or patent application. In a further approach, the search query includes at least a portion of a summary from a patent or patent application.

Figure 27:
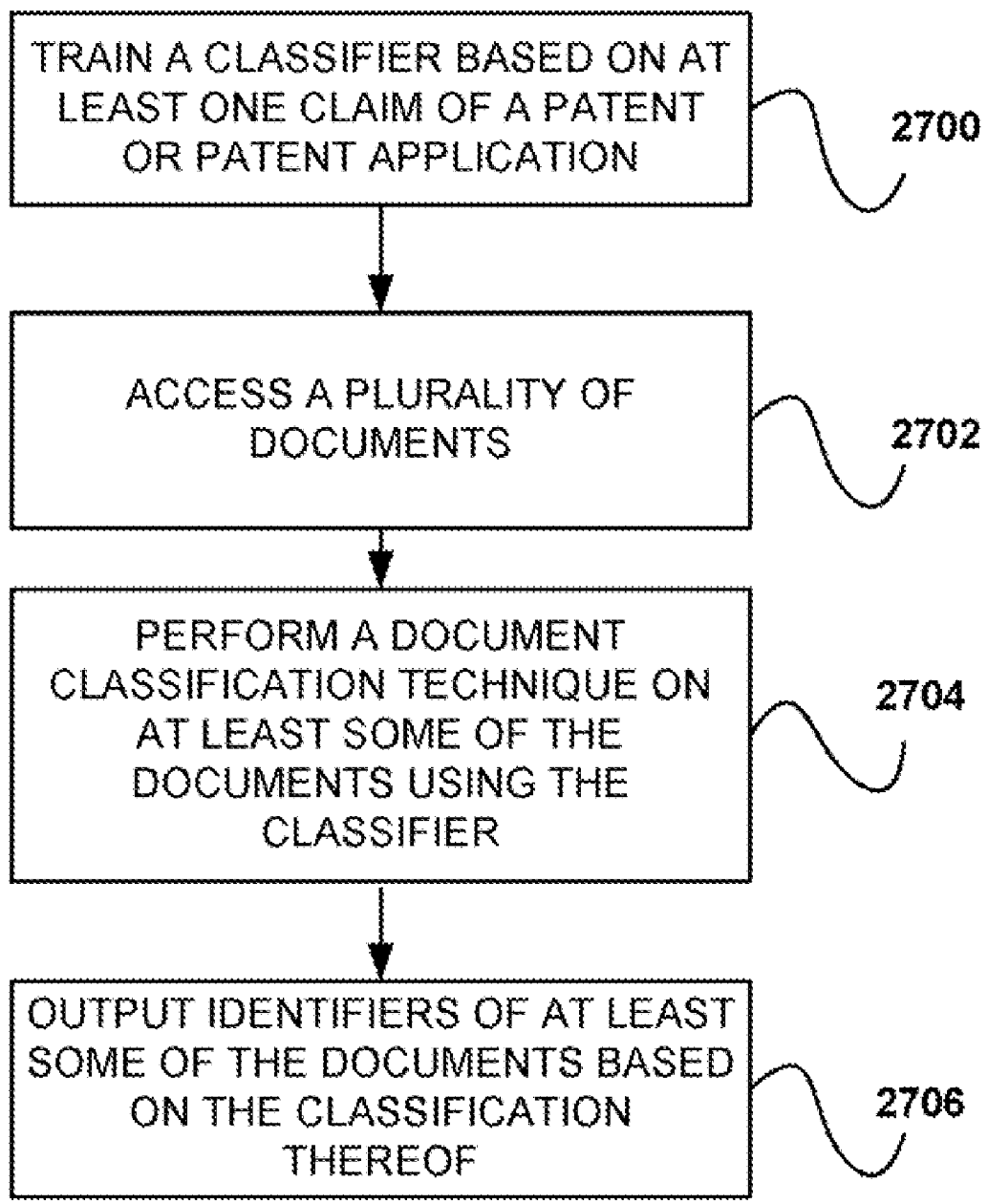
FIG. 27 illustrates, in a flowchart, a classification process performed by in accordance with one embodiment.

FIG. 27 illustrates a method for matching documents to claims. In step 2700, a classifier is trained based on at least one claim of a patent or patent application. Thus, one or more claims, or a portion thereof, may be used to train the classifier. In step 2702, a plurality of documents are accessed. Such documents may include prior art documents, documents describing potentially infringing or anticipating products, etc. In step 2704, a document classification technique is performed on at least some of the documents using the classifier. In step 2706, identifiers of at least some of the documents are output based on the classification thereof. A relevance score of at least some of the documents may also be output based on the classification thereof.

An embodiment of the present invention may be used for the classification of patent applications. In the United States, for example, patents and patent applications are currently classified by subject matter using the United States Patent Classification (USPC) system. This task is currently performed manually, and therefore is very expensive and time consuming. Such manual classification is also subject to human errors. Compounding the complexity of such a task is that the patent or patent application may be classified into multiple classes.

Figure 28:
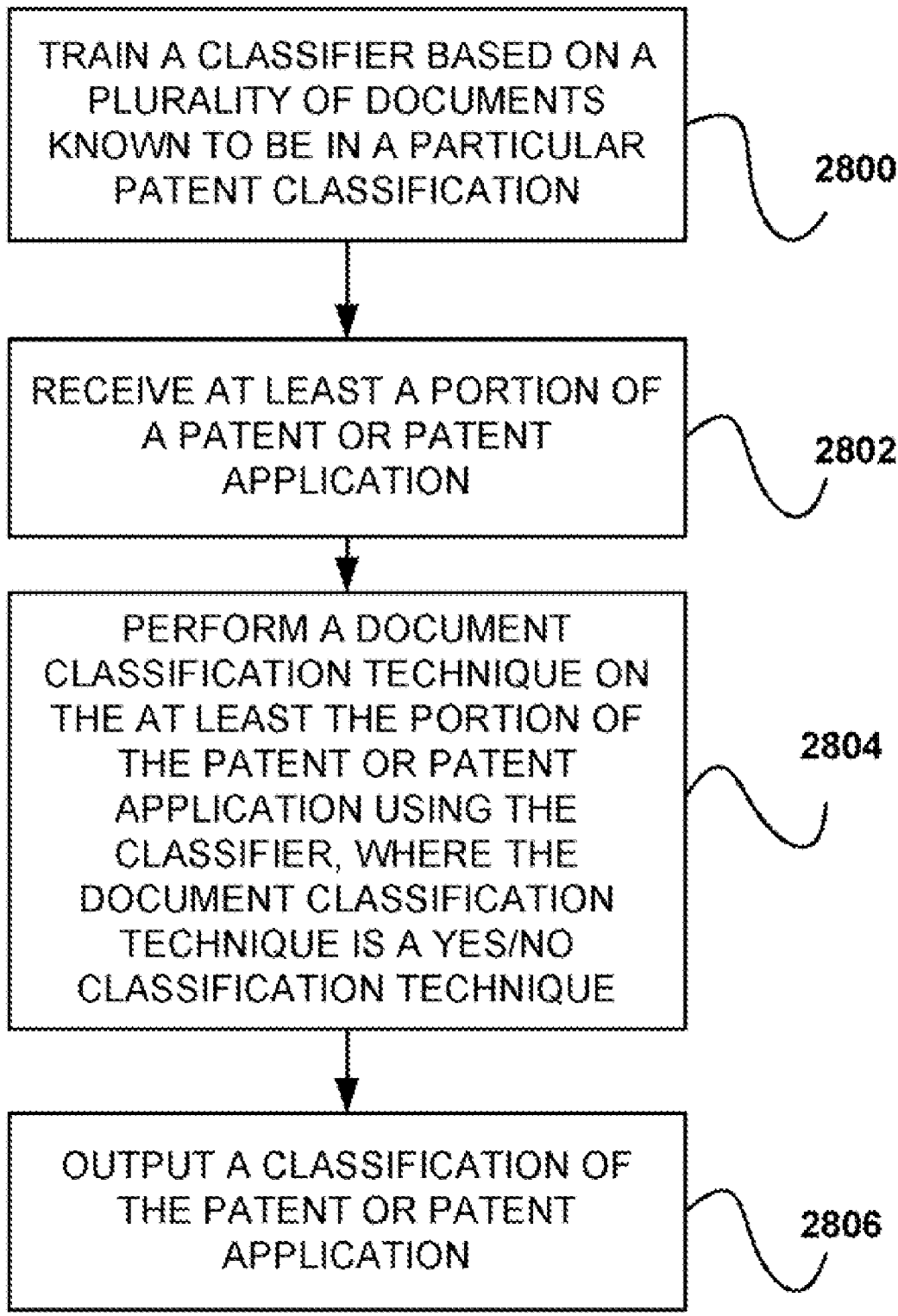
FIG. 28 illustrates, in a flowchart, a classification process performed by in accordance with one embodiment.

FIG. 28 depicts a method for classifying a patent application according to one embodiment. In step 2800, a classifier is trained based on a plurality of documents known to be in a particular patent classification. Such documents may typically be patents and patent applications (or portions thereof), but could also be summary sheets describing target subject matter of the particular patent classification. In step 2802, at least a portion of a patent or patent application is received. The portion may include the claims, summary, abstract, specification, title, etc. In step 2804, a document classification technique is performed on the at least the portion of the patent or patent application using the classifier. In step 2806, a classification of the patent or patent application is output. As an option, a user may manually verify the classification of some or all of the patent applications.

The document classification technique is preferably a yes/no classification technique. In other words, if the probability that the document is in the proper class is above a threshold, the decision is yes, the document belongs in this class. If the probability that the documents is in the proper class is below a threshold, the decision is no, the document does not belong in this class.

Figure 29:
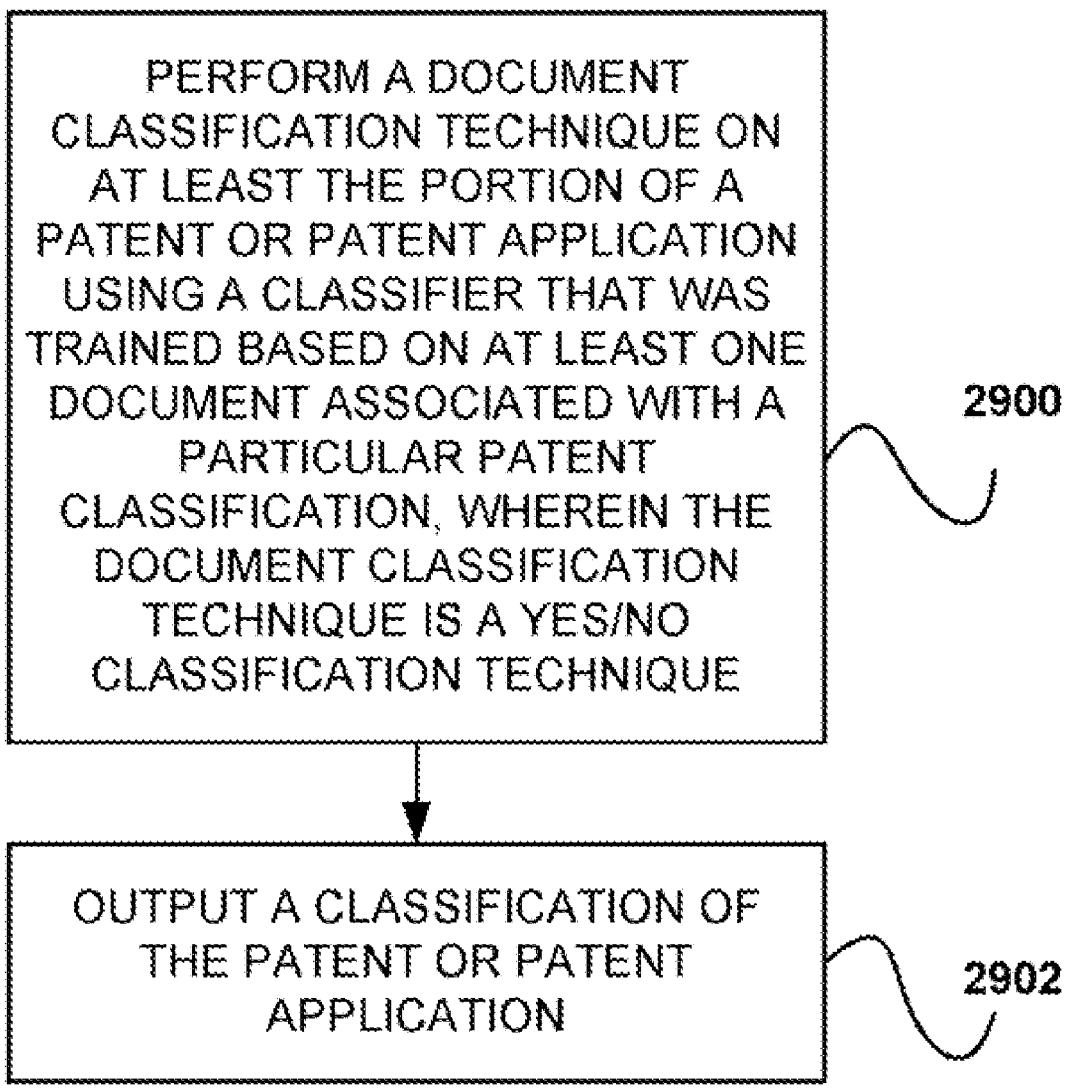
FIG. 29 illustrates, in a flowchart, a classification process performed by in accordance with one embodiment.

FIG. 29 depicts yet another method for classifying a patent application. In step 2900, a document classification technique is performed on at least the portion of a patent or patent application using a classifier that was trained based on at least one document associated with a particular patent classification. Again, the document classification technique is preferably a yes/no classification technique. In step 2902, a classification of the patent or patent application is output.

In either of the methods shown in FIGS. 28 and 29, the respective method may be repeated using a different classifier that was trained based on a plurality of documents known to be in a different patent classification.

Officially, classification of a patent should be based on the claims. However, it may also be desirable to perform matching between (any IP related content) and (any IP related content). As an example, one approach uses the Description of a patent to train, and classify an application based on its Claims. Another approach uses the Description and Claims to train, and classify based on the Abstract. In particularly preferred approaches, whatever portion of a patent or application is used to train, that same type of content is used when classifying, i.e., if the system is trained on claims, the classification is based on claims.

The document classification technique may include any type of process, e.g. a transductive process, etc. For example, any inductive or transductive technique described above may be used. In a preferred approach, the classifier may be a transductive classifier, and the transductive classifier may be trained through iterative calculation using at least one predetermined cost factor, at least one seed document, and the prior art documents, wherein for each iteration of the calculations the cost factor is adjusted as a function of an expected label value, and the trained classifier may be used to classify the prior art documents. A data point label prior probability for the seed document and prior art documents may also be received, wherein for each iteration of the calculations the data point label prior probability may be adjusted according to an estimate of a data point class membership probability. The seed document may be any document, e.g. publications of a patent office, data retrieved from a database, a collection of prior art, a website, a patent disclosure, etc.

Figure 14:
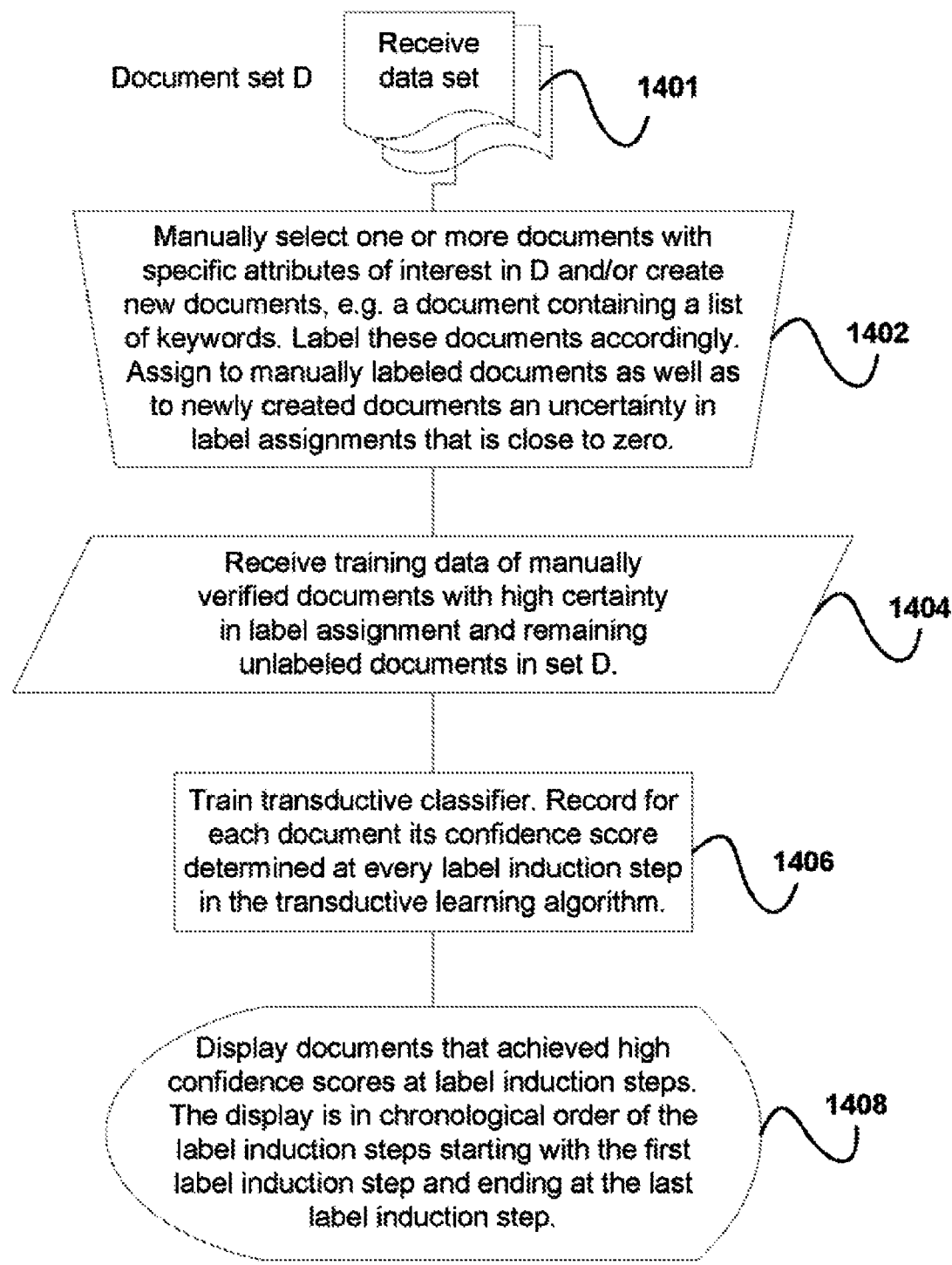
FIG. 14 illustrates, in a flowchart, a classification process performed by in accordance with one embodiment.

In one approach, FIG. 14 describes one embodiment of the present invention. In step 1401, a set of data is read. The discovery of documents within this set that are relevant to the user is desired. In step 1402 an initial seed document or documents are labeled. The documents may be any type of documents, e.g. publications of a patent office, data retrieved from a database, a collection of prior art, a website, etc. It is also possible to seed the transduction process with a string of different key words or a document provided by the user. In step 1406 training a transductive classifier is trained using the labeled data as well as the set of unlabeled data in the given set. At each label induction step during the iterative transduction process the confidence scores determined during label induction are stored. Once training is finished, the documents that achieved high confidence scores at the label induction steps are displayed in step 1408 for the user. These documents with high confidence scores represent documents relevant to the user for purposes of discovery. The display may be in chronological order of the label induction steps starting with the initial seed document to the final set of documents discovered at the last label induction step.

Another embodiment of the present invention involves data cleanup and accurate classification, for example in conjunction with the automation of business processes. The cleanup and classification technique may include any type of process, e.g. a transductive process, etc. For example, any inductive or transductive technique described above may be used. In a preferred approach, the keys of the entries in the database are utilized as labels associated with some confidence level according to the expected cleanliness of the database. The labels together with the associated confidence level, i.e. the expected labels, are then used to train a transductive classifier that corrects the labels (keys) in order to achieve a more consistent organization of the data in the database. For example, invoices have to be first classified according to the company or person that originated the invoice in order to enable automatic data extraction, e.g. the determination of total dollar amount, purchase order number, product amount, shipping address, etc. Commonly, training examples are needed to set up an automatic classification system. However, training examples provided by the customer often contain misclassified documents or other noise—e.g. fax cover sheets—that have to be identified and removed prior to training the automatic classification system in order to obtain accurate classification. In another example, in the area of patient records, it is useful to detect inconsistencies between the report written by the physician and the diagnosis.

In another example, it is known that the Patent Office undergoes a continuous reclassification process, in which they (1) evaluate an existing branch of their taxonomy for confusion, (2) re-structure that taxonomy to evenly distributed overly congested nodes, and (3) reclassify existing patents into the new structure. The transductive learning methods presented herein may be used by the Patent Office, and the companies they outsource to do this work, to revaluate their taxonomy, and assist them in (1) build a new taxonomy for a given main classification, and (2) reclassifying existing patents.

Transduction learns from labeled and unlabeled data, whereby the transition from labeled to unlabeled data is fluent. At one end of the spectrum are labeled data with perfect prior knowledge, i.e. the given labels are correct with no exceptions. At the other end are unlabeled data where no prior knowledge is given. Organized data with some level of noise constitute mislabeled data and are located somewhere on the spectrum between these two extremes: The labels given by the organization of the data can be trusted to be correct to some extent but not fully. Accordingly, transduction can be utilized to clean up the existing organization of data by assuming a certain level of mistakes within the given organization of the data and interpreting these as uncertainties in the prior knowledge of label assignments.

Figure 15:
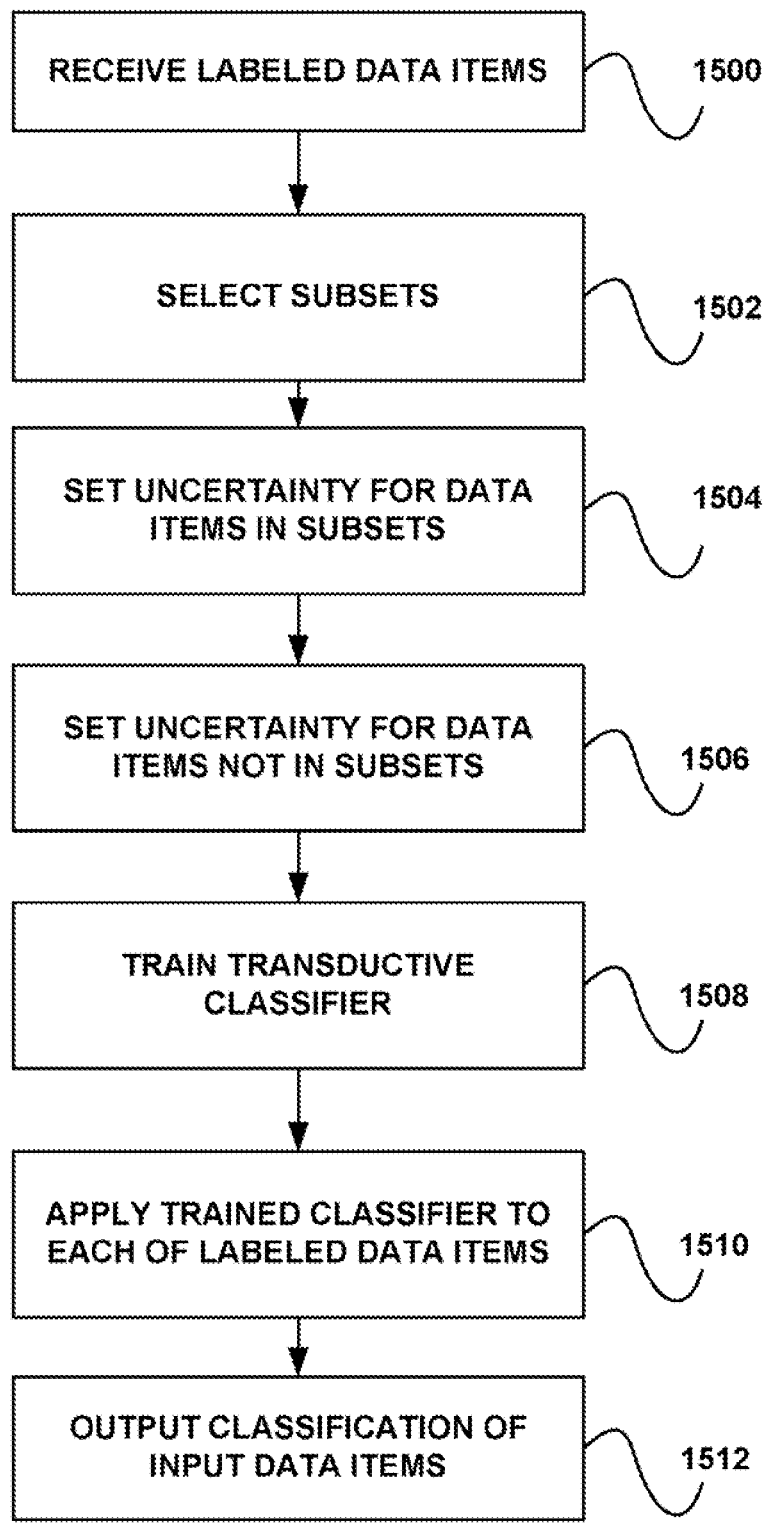
FIG. 15 illustrates, in a flowchart, a classification process performed by in accordance with one embodiment.

In one embodiment, a method for cleaning up data is presented in FIG. 15. In use, a plurality of labeled data items are received in step 1500, and subsets of the data items for each of a plurality of categories are selected in step 1502. Additionally, an uncertainty for the data items in each subset is set in step 1504 to about zero, and an uncertainty for the data items not in the subsets is set in step 1506 to a predefined value that is not about zero. Further, a transductive classifier is trained in step 1508 through iterative calculation using the uncertainties, the data items in the subsets, and the data items not in the subsets as training examples, and the trained classifier is applied to each of the labeled data items in step 1510 to classify each of the data items. Also, a classification of the input data items, or derivative thereof, is output in step 1512 to at least one of a user, another system, and another process.

Further, the subsets may be selected at random and may be selected and verified by a user. The label of at least some of the data items may be changed based on the classification. Also, identifiers of data items having a confidence level below a predefined threshold after classification thereof may be output to a user. The identifiers may be electronic copies of the document themselves, portions thereof, titles thereof, names thereof, file names thereof, pointers to the documents, etc.

Figure 16:
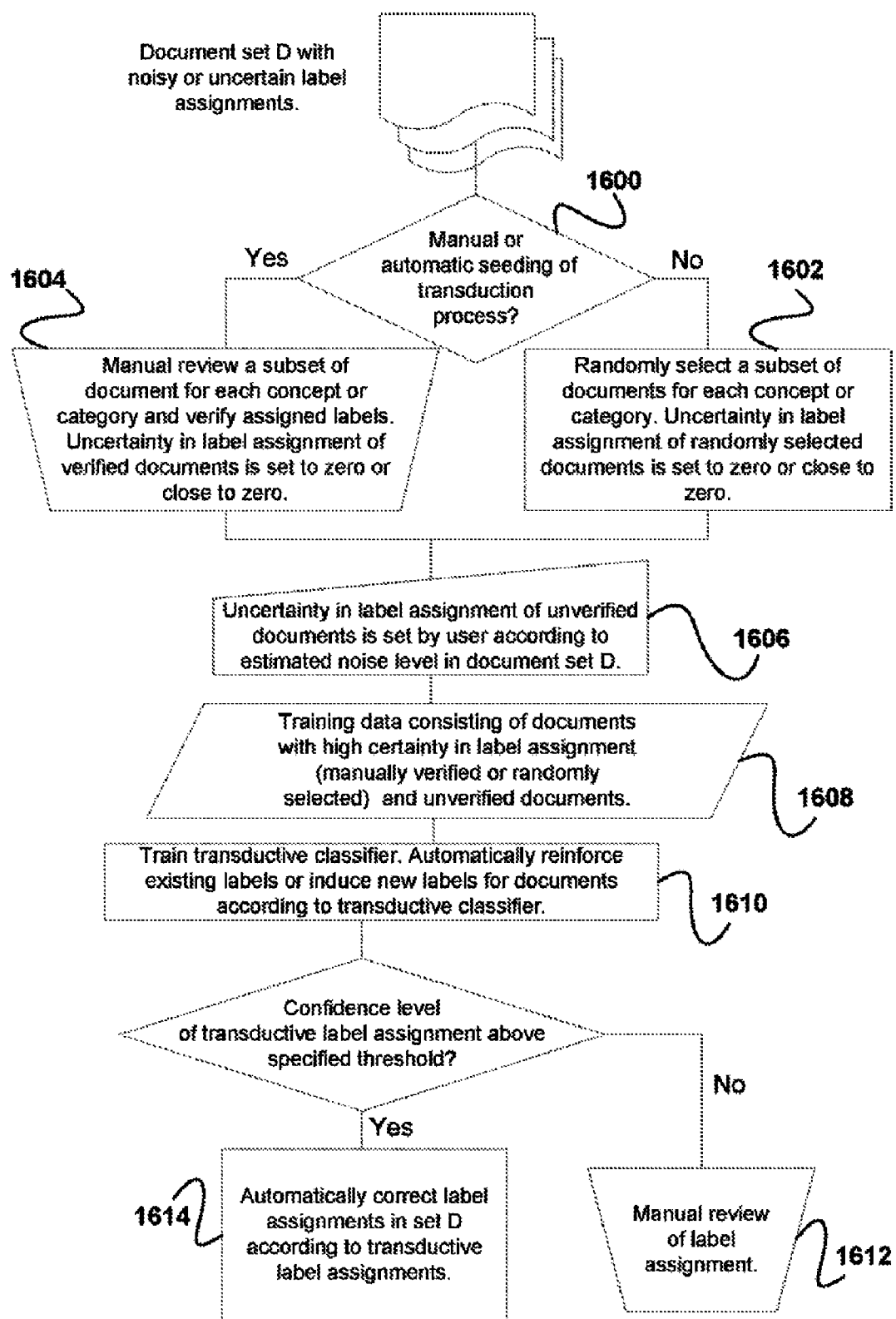
FIG. 16 illustrates, in a flowchart, a classification process performed by in accordance with one embodiment.

In one embodiment of the present invention, as illustrated in FIG. 16, two choices to start a cleanup process are presented to the user at step 1600. One choice is fully automatic cleanup at step 1602, where for each concept or category a specified number of documents are randomly selected and assumed to be correctly organized. Alternatively, at step 1604 a number of documents can be flagged for manual review and verification that one or more label assignments for each concept or category is being correctly organized. An estimate of the noise level in the data is received at step 1606. The transductive classifier is trained in step 1610 using the verified (manually verified or randomly selected) data and the unverified data in step 1608. Once training is finished the documents are reorganized according to the new labels. Documents with low confidence levels in their label assignments below a specified threshold are displayed for the user for manual review in step 1612. Documents with confidence levels in their label assignments above a specified threshold are automatically corrected according to transductive label assignments in step 1614.

Figure 17:
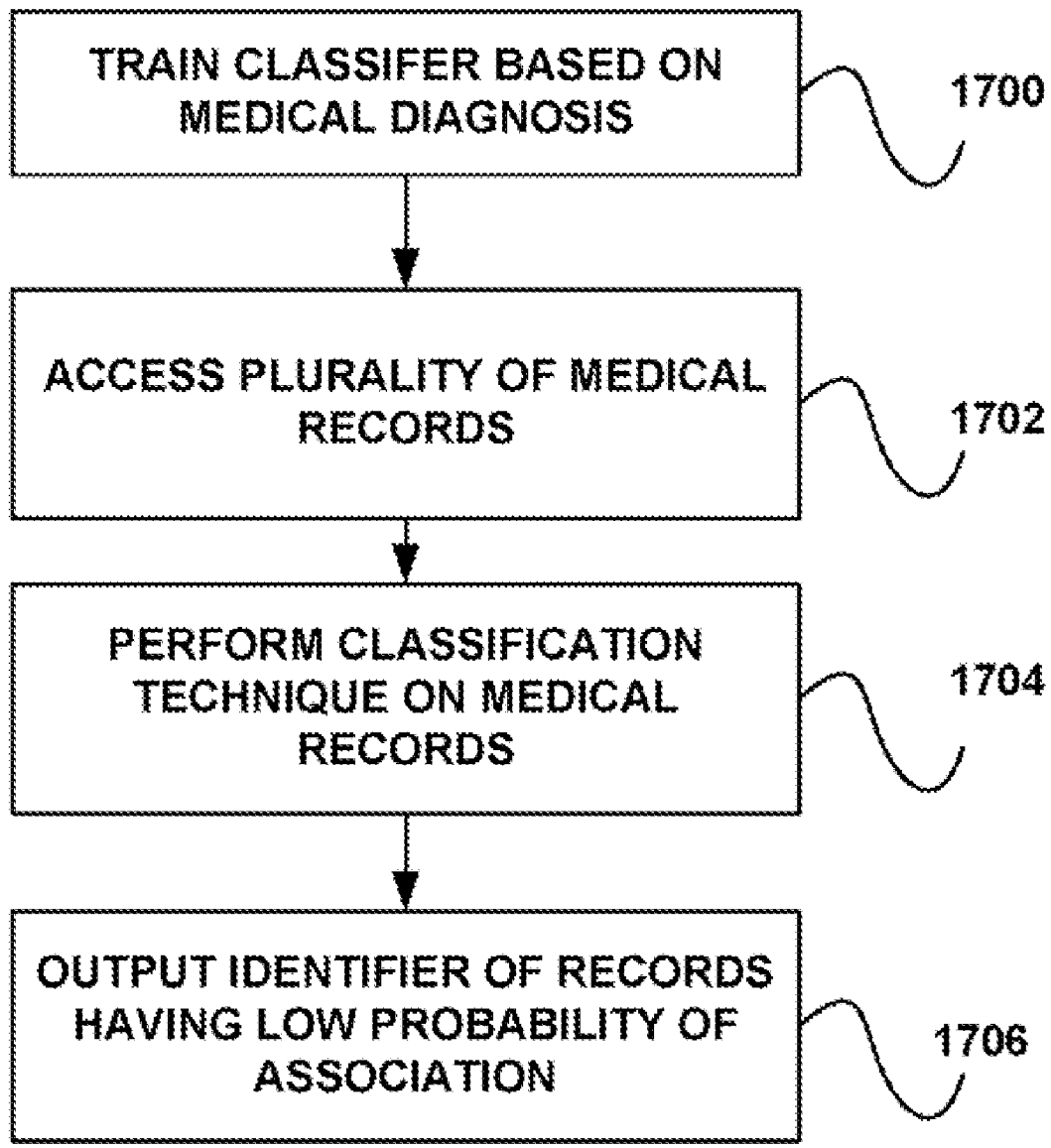
FIG. 17 illustrates, in a flowchart, a classification process performed by in accordance with one embodiment.

In another embodiment, a method for managing medical records is presented in FIG. 17. In use, a classifier is trained based on a medical diagnosis in step 1700, and a plurality of medical records is accessed in step 1702. Additionally, a document classification technique is performed on the medical records in step 1704 using the classifier, and an identifier of at least one of the medical records having a low probability of being associated with the medical diagnosis is output in step 1706. The document classification technique may include any type of process, e.g. a transductive process, etc., and may include one or more of any inductive or transductive technique described above, including a support vector machine process, a maximum entropy discrimination process, etc.

In one embodiment, the classifier may be a transductive classifier, and the transductive classifier may be trained through iterative calculation using at least one predetermined cost factor, at least one seed document, and the medical records, wherein for each iteration of the calculations the cost factor is adjusted as a function of an expected label value, and the trained classifier may be used to classify the medical records. A data point label prior probability for the seed document and medical records may also be received, wherein for each iteration of the calculations the data point label prior probability may be adjusted according to an estimate of a data point class membership probability.

Another embodiment of the present invention accounts for dynamic, shifting classification concepts. For example, in forms processing applications documents are classified using the layout information and/or the content information of the documents to classify the documents for further processing. In many applications the documents are not static but evolve over time. For example the content and/or layout of a document may change owing to new legislation. Transductive classification adapts to these changes automatically yielding the same or comparable classification accuracy despite the drifting classification concepts. This is in contrast to rule based systems or inductive classification methods that, without manually adjustments, will start to suffer in classification accuracy owing to the concept drift. One example of this is invoice processing, which traditionally involves inductive learning, or rule-based systems are used that utilize invoice layout. Under these traditional systems, if a change in the layout occurs the systems have to be manually reconfigured by either labeling new training data or by determining new rules. However, the use of transduction makes the manual reconfiguration unnecessary by automatically adapting to the small changes in layout of the invoices. In another example, transductive classification may be applied to the analysis of customer complaints in order to monitor the changing nature of such complaints. For example, a company can automatically link product changes with customer complaints.

Transduction may also be used in the classification of news articles. For example, news articles on the war on terror starting with articles about the terrorist attacks on Sep. 11, 2001 over the war in Afghanistan to news stories about the situation in today's Iraq can be automatically identified using transduction.

In yet another example, the classification of organisms (alpha taxonomy) can change over time through evolution by creating new species of organisms and other species becoming extinct. This and other principles of a classification schema or taxonomy can be dynamic, with classification concepts shifting or changing over time.

Figure 18:
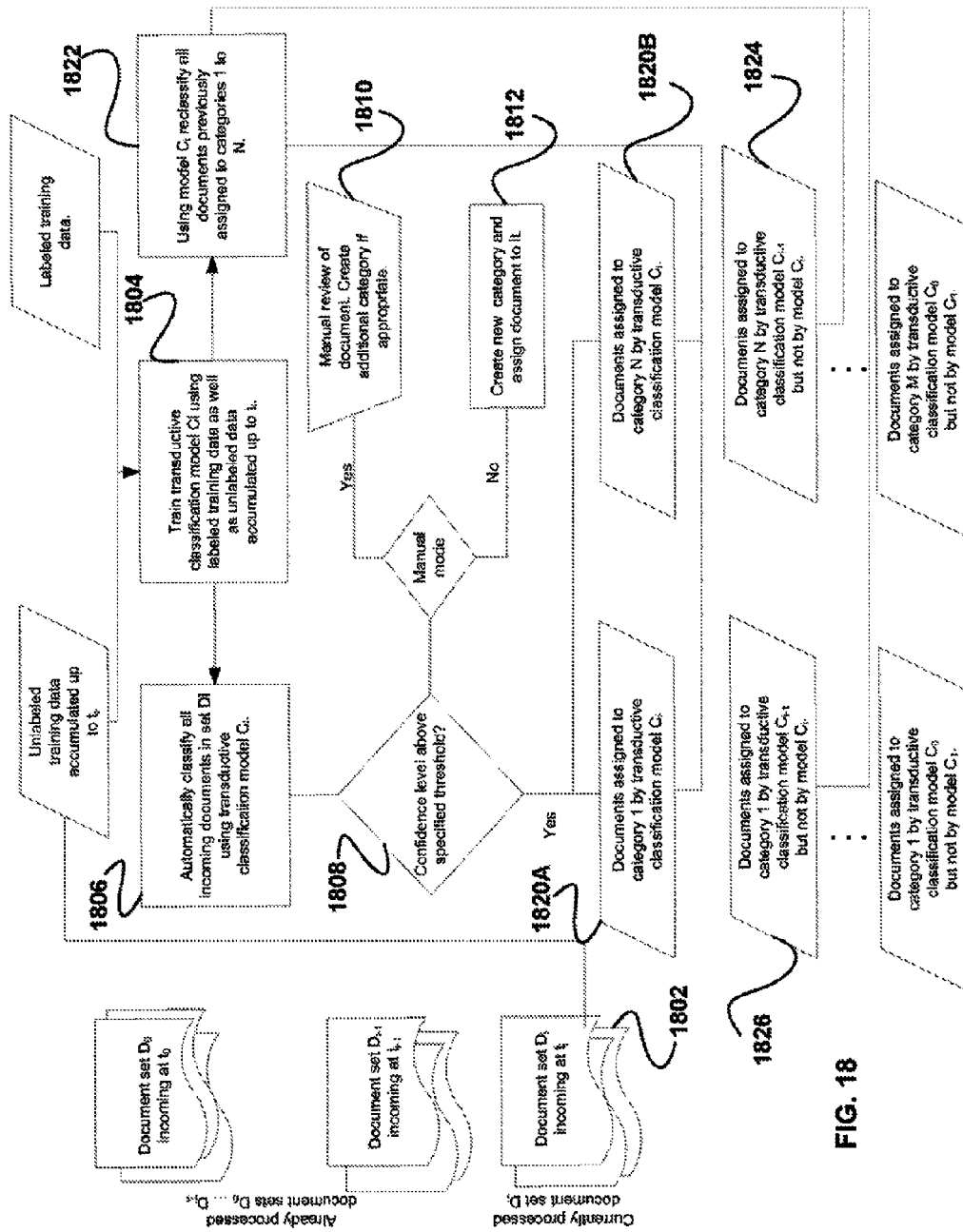
FIG. 18 illustrates, in a flowchart, a classification process performed by in accordance with one embodiment.

By using the incoming data that have to be classified as unlabeled data, transduction can recognize shifting classification concepts, and therefore dynamically adapt to the evolving classification schema. For example, FIG. 18 shows an embodiment of the invention using transduction given drifting classification concepts. Document set $D_i$ enters the system at time $t_i$, as shown in step 1802. At step 1804 a transductive classifier $C_i$ is trained using labeled data and the unlabeled data accumulated so far, and in step 1806 the documents in set $D_i$ are classified. If the manual mode is used, documents with a confidence level below a user supplied threshold as determined in step 1808 are presented to the user for manual review in step 1810. As shown in step 1812, in the automatic mode a document with a confidence level triggers the creation of a new category that is added to the system, and the document is then assigned to the new category. Documents with a confidence level above the chosen threshold are classified into the current categories 1 to N in steps 1820A-B. All documents in the current categories that have been classified prior to step $t_1$ into the current categories are reclassified by the classifier $C_i$ in step 1822, and all documents that are no longer classified into the previously assigned categories are moved to new categories in steps 1824 and 1826.

Figure 19:
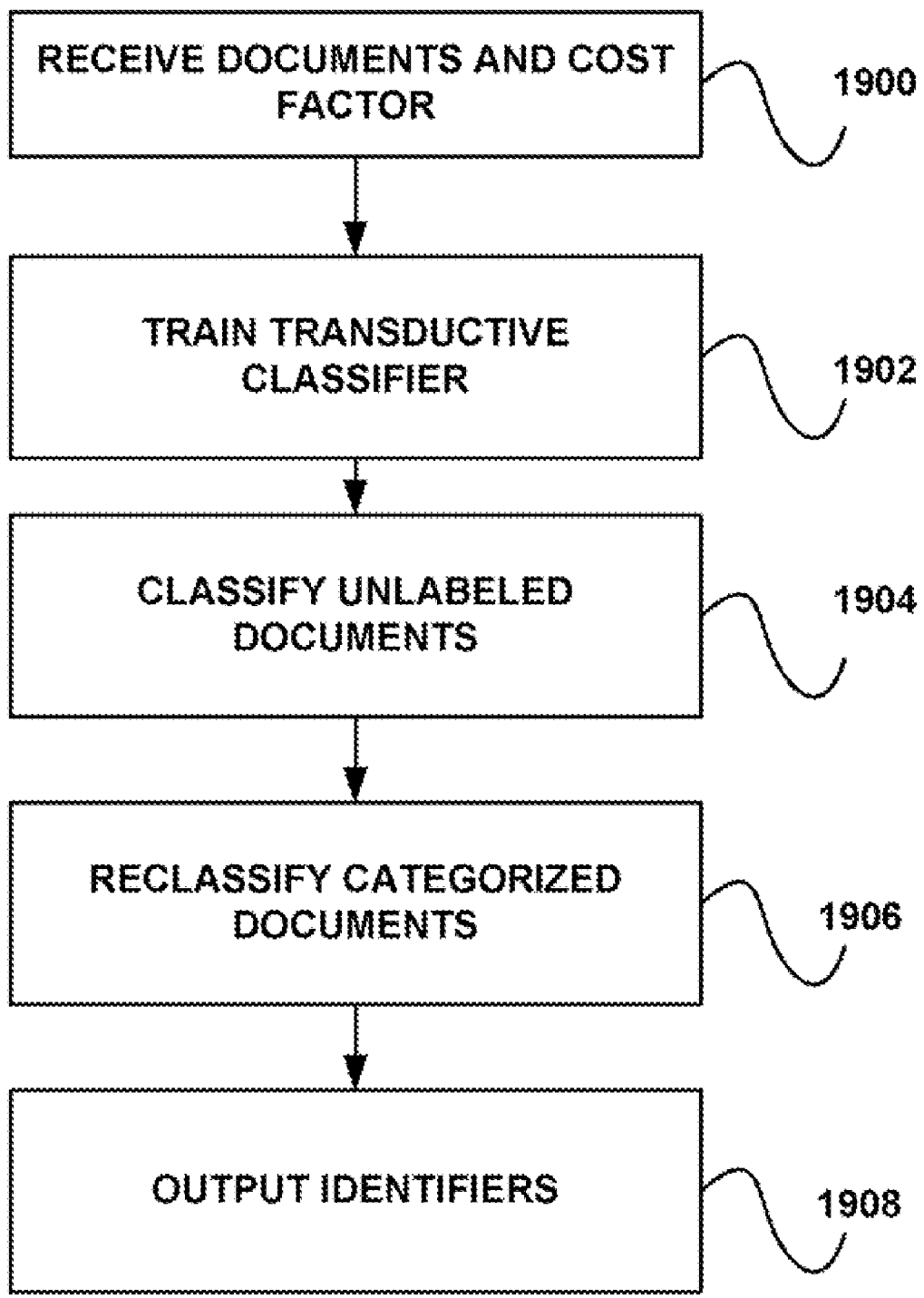
FIG. 19 illustrates, in a flowchart, a classification process performed by in accordance with one embodiment.

In yet another embodiment, a method for adapting to a shift in document content is presented in FIG. 19. Document content may include, but is not limited to, graphical content, textual content, layout, numbering, etc. Examples of shift may include temporal shift, style shift (where 2 or more people work on one or more documents), shift in process applied, shift in layout, etc. In step 1900, at least one labeled seed document is received, as well as unlabeled documents and at least one predetermined cost factor. The documents may include, but are not limited to, customer complaints, invoices, form documents, receipts, etc. Additionally, a transductive classifier is trained in step 1902 using the at least one predetermined cost factor, the at least one seed document, and the unlabeled documents. Also, in step 1904 the unlabeled documents having a confidence level above a predefined threshold are classified into a plurality of categories using the classifier, and at least some of the categorized documents are reclassified in step 1906 into the categories using the classifier. Further, identifiers of the categorized documents are output in step 1908 to at least one of a user, another system, and another process. The identifiers may be electronic copies of the document themselves, portions thereof titles thereof, names thereof, file names thereof, pointers to the documents, etc. Further, product changes may be linked with customer complaints, etc.

In addition, an unlabeled document having a confidence level below the predefined threshold may be moved into one or more new categories. Also, the transductive classifier may be trained through iterative calculation using at least one predetermined cost factor, the at least one seed document, and the unlabeled documents, wherein for each iteration of the calculations the cost factor may be adjusted as a function of an expected label value, and using the trained classifier to classify the unlabeled documents. Further, a data point label prior probability for the seed document and unlabeled documents may be received, wherein for each iteration of the calculations the data point label prior probability may be adjusted according to an estimate of a data point class membership probability.

Figure 20:
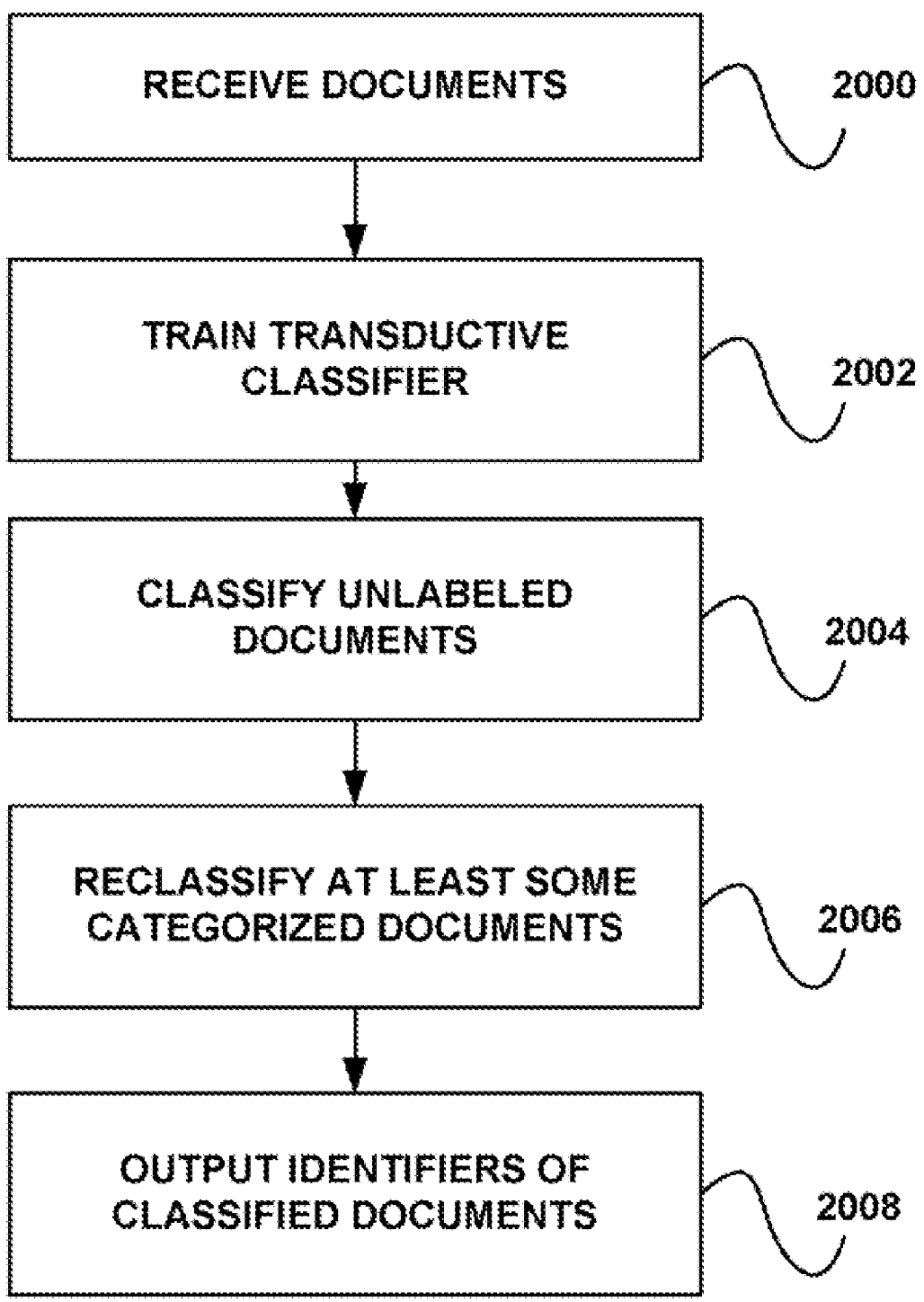
FIG. 20 illustrates, in a flowchart, a classification process performed by in accordance with one embodiment.

In another embodiment, a method for adapting a patent classification to a shift in document content is presented in FIG. 20. In step 2000, at least one labeled seed document is received, as well as unlabeled documents. The unlabeled documents may include any types of documents, e.g. patent applications, legal filings, information disclosure forms, document amendments, etc. The seed document(s) may include patent(s), patent application(s), etc. A transductive classifier is trained in step 2002 using the at least one seed document and the unlabeled documents, and the unlabeled documents having a confidence level above a predefined threshold are classified into a plurality of existing categories using the classifier. The classifier may be any type of classifier, e.g. a transductive classifier, etc., and the document classification technique may be any technique, e.g. a support vector machine process, a maximum entropy discrimination process, etc. For example, any inductive or transductive technique described above may be used.

Also, in step 2004 the unlabeled documents having a confidence level below the predefined threshold are classified into at least one new category using the classifier, and at least some of the categorized documents are reclassified in step 2006 into the existing categories and the at least one new category using the classifier. Further, identifiers of the categorized documents are output in step 2008 to at least one of a user, another system, and another process. Also, the transductive classifier may be trained through iterative calculation using at least one predetermined cost factor, the search query, and the documents, wherein for each iteration of the calculations the cost factor may be adjusted as a function of an expected label value, and the trained classifier may be used to classify the documents. Further, a data point label prior probability for the search query and documents may be received, wherein for each iteration of the calculations the data point label prior probability is adjusted according to an estimate of a data point class membership probability.

Yet another embodiment of the present invention accounts for document drift in the field of document separation. One use case for Document separation involves the processing of mortgage documents. Loan folders consisting of a sequence of different loan documents, e.g. loan applications, approvals, requests, amounts, etc. are scanned and the different documents within the sequence of images have to be determined before further processing. The documents used are not static but can change over time. For example, tax forms used within a loan folder can change over time owing to legislation changes.

Document separation solves the problem of finding document or subdocument boundaries in a sequence of images. Common examples that produce a sequence of images are digital scanners or Multi Functional Peripherals (MFPs). As in the case of classification, transduction can be utilized in Document separation in order to handle the drift of documents and their boundaries over time. Static separation systems like rule based systems or systems based on inductive learning solutions cannot adapt automatically to drifting separation concepts. The performance of these static separation systems degrade over time whenever a drift occurs. In order to keep the performance on its initial level, one either has to manually adapt the rules (in the case of a rule based system), or has to manually label new documents and relearn the system (in case of an inductive learning solution). Either way is time and cost expensive. Applying transduction to Document separation allows the development of a system that automatically adapts to the drift in the separation concepts.

Figure 21:
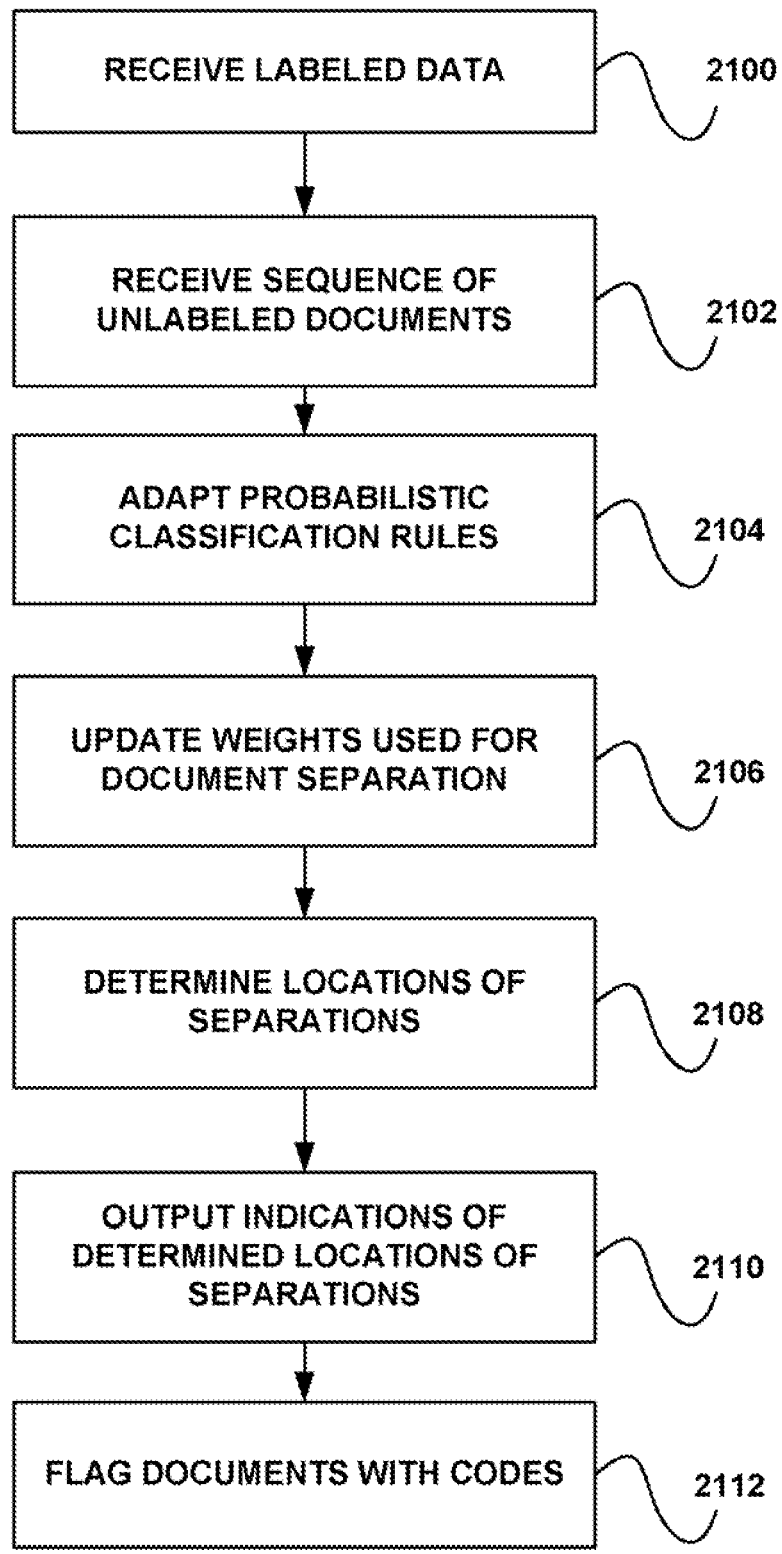
FIG. 21 illustrates, in a flowchart, a classification process performed by in accordance with one embodiment.

In one embodiment, a method for separating documents is presented in FIG. 21. In step 2100, labeled data are received, and in step 2102 a sequence of unlabeled documents is received. Such data and documents may include legal discovery documents, office actions, web page data, attorney-client correspondence, etc. In addition, in step 2104 probabilistic classification rules are adapted using transduction based on the labeled data and the unlabeled documents, and in step 2106 weights used for document separation are updated according to the probabilistic classification rules. Also, in step 2108 locations of separations in the sequence of documents are determined, and in step 2110 indicators of the determined locations of the separations in the sequence are output to at least one of a user, another system, and another process. The indicators may be electronic copies of the document themselves, portions thereof, titles thereof, names thereof, file names thereof, pointers to the documents, etc. Further, in step 2112 the documents are flagged with codes, the codes correlating to the indicators.

Figure 22:
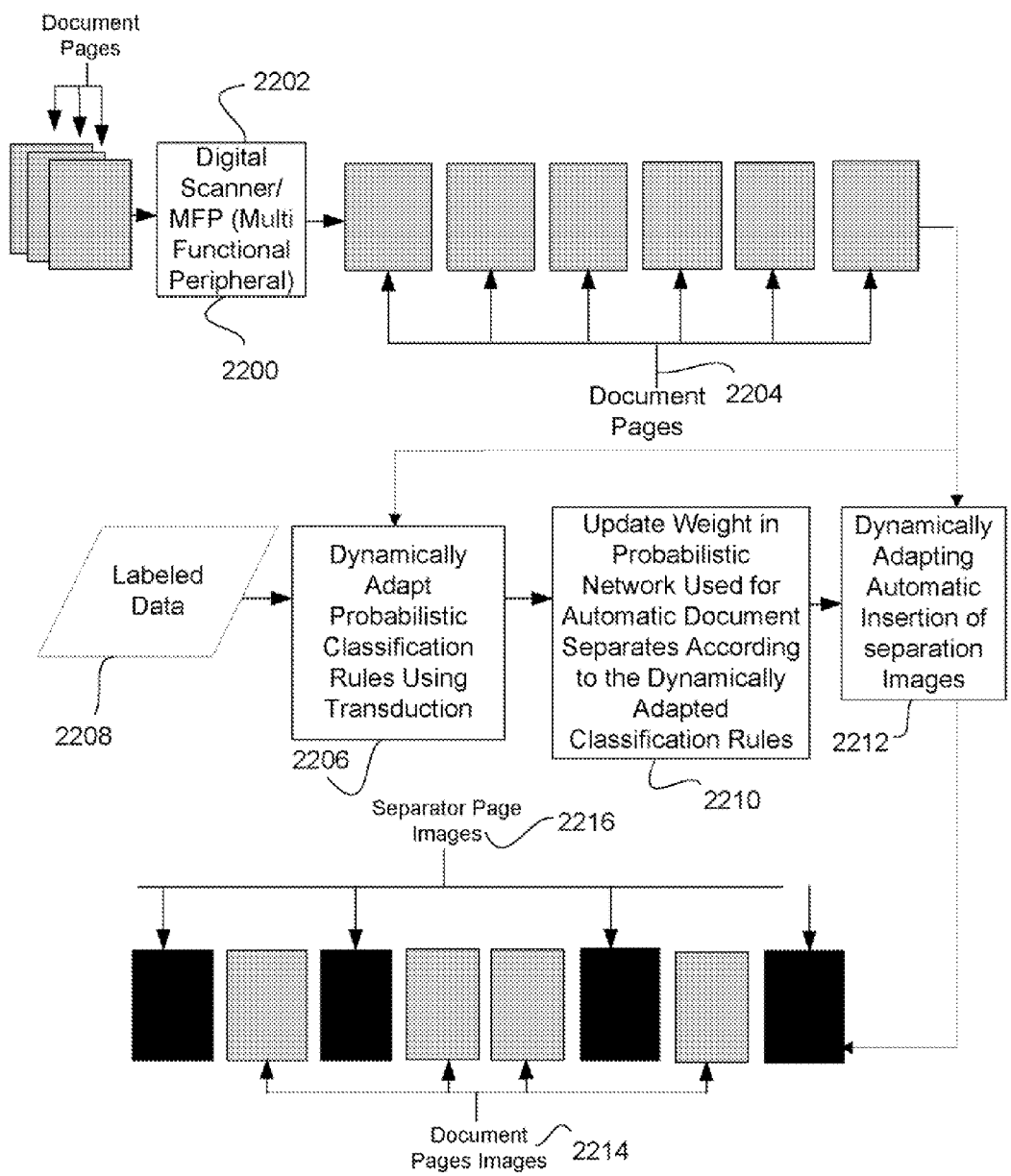
FIG. 22 illustrates a control flow diagram showing the method of one embodiment of the present invention applied to a first document separating system.

FIG. 22 shows an implementation of the classification method and apparatus of the present invention used in association with document separation. Automatic document separation is used for reducing the manual effort involved in separating and identifying documents after digital scanning One such document separation method and apparatus is described in U.S. Publication 2005/0134935 published Jun. 23, 2005 to Schmidtler et al, the substance of which is incorporated herein by reference. In the aforementioned publication, the method combined classification rules to automatically separate sequences of pages by using inference algorithms to reduce the most likely separation from all of the available information, using the classifications methods described therein. In one embodiment of the present invention as shown in FIG. 22, the classification method of transductive MED of the present invention is employed in document separation. More particularly, document pages 2200 are inserted into a digital scanner 2202 or MFP and are converted into a sequence of digital images 2204. The document pages may be pages from any type of document, e.g. publications of a patent office, data retrieved from a database, a collection of prior art, a website, etc. The sequence of digital images is input at step 2206 to dynamically adapt probabilistic classification rules using transduction. Step 2206 utilizes the sequence of images 2204 as unlabeled data and labeled data 2208. At step 2210 the weight in the probabilistic network is updated and is used for automatic document separation according to dynamically adapted classification rules. The output step 2212 is a dynamic adaptation of automatic insertion of separation images such that a sequence of digitized pages 2214 is interleaved with automatic images of separator sheets 2216 at step 2212 automatically inserts the separator sheet images into the image sequence. In one embodiment of the invention, the software generated separator pages 2216 may also indicate the type of document that immediately follows or proceeds the separator page 2216. The system described here automatically adapts to drifting separation concepts of the documents that occur over time without suffering from a decline in separation accuracy as would static systems like rule based or inductive machine learning based solutions. A common example for drifting separation or classification concepts in form processing applications are, as mentioned earlier, changes to documents owing to new legislation.

Figure 23:
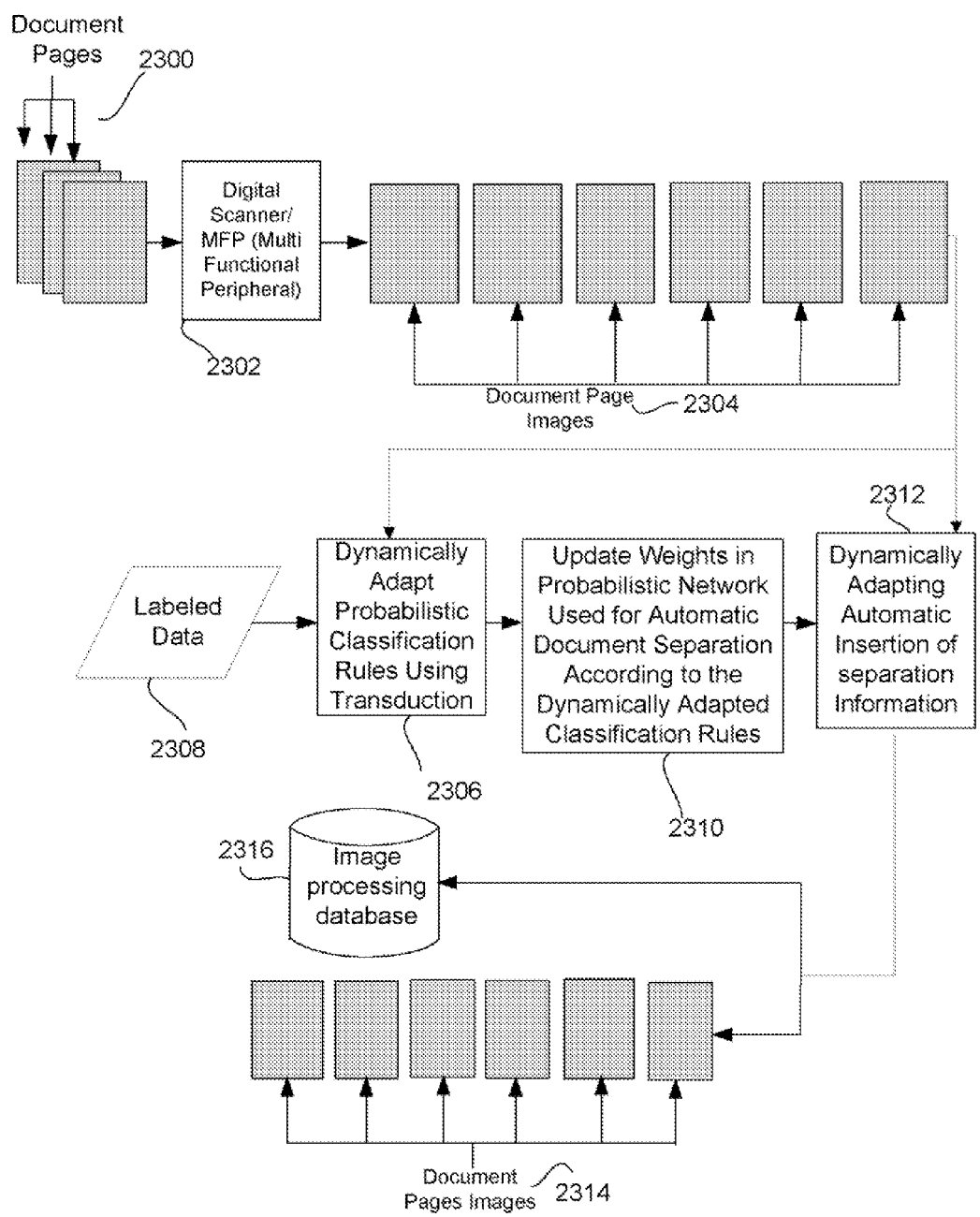
FIG. 23 illustrates a control flow diagram showing the method of one embodiment of the present invention applied to a second separating system.

Additionally, the system as shown in FIG. 22 may be modified to a system as shown in FIG. 23 where the pages 2300 are inserted into a digital scanner 2302 or MFP converted into a sequence of digital images 2304. The sequence of digital images is input at step 2306 to dynamically adapt probabilistic classification rules using transduction. Step 2306 utilizes the sequence of images 2304, as unlabeled data and labeled data 2308. Step 2310 updates weights in the probabilistic network used for automatic document separation according to dynamically adapted classification rules employed. In step 2312 instead of inserting separator sheet images as described in FIG. 18, step 2312 dynamically adapts the automated insertion of separation information and flags the document images 2314 with a coded description. Thus the document page images can be input into an imaging processed database 2316 and the documents can be accessed by the software identifiers.

Yet another embodiment of the present invention is able to perform face recognition using transduction. As mentioned above, the use of transduction has many advantages, for example the need of a relatively small number of training examples, the ability to use unlabeled examples in training, etc. By making use of the aforementioned advantages, transductive face recognition may be implemented for criminal detection.

For example, the Department of Homeland Security must ensure that terrorists are not allowed onto commercial airliners. Part of an airport's screening process may be to take a picture of each passenger at the airport security checkpoint and attempt to recognize that person. The system could initially be trained using a small number of examples from the limited photographs available of possible terrorists. There may also be more unlabeled photographs of the same terrorist available in other law-enforcement databases that may also be used in training. Thus, a transductive trainer would take advantage of not only the initially sparse data to create a functional face-recognition system but would also use unlabeled examples from other sources to increase performance. After processing the photograph taken at the airport security checkpoint, the transductive system would be able to recognize the person in question more accurately than a comparable inductive system.

Figure 24:
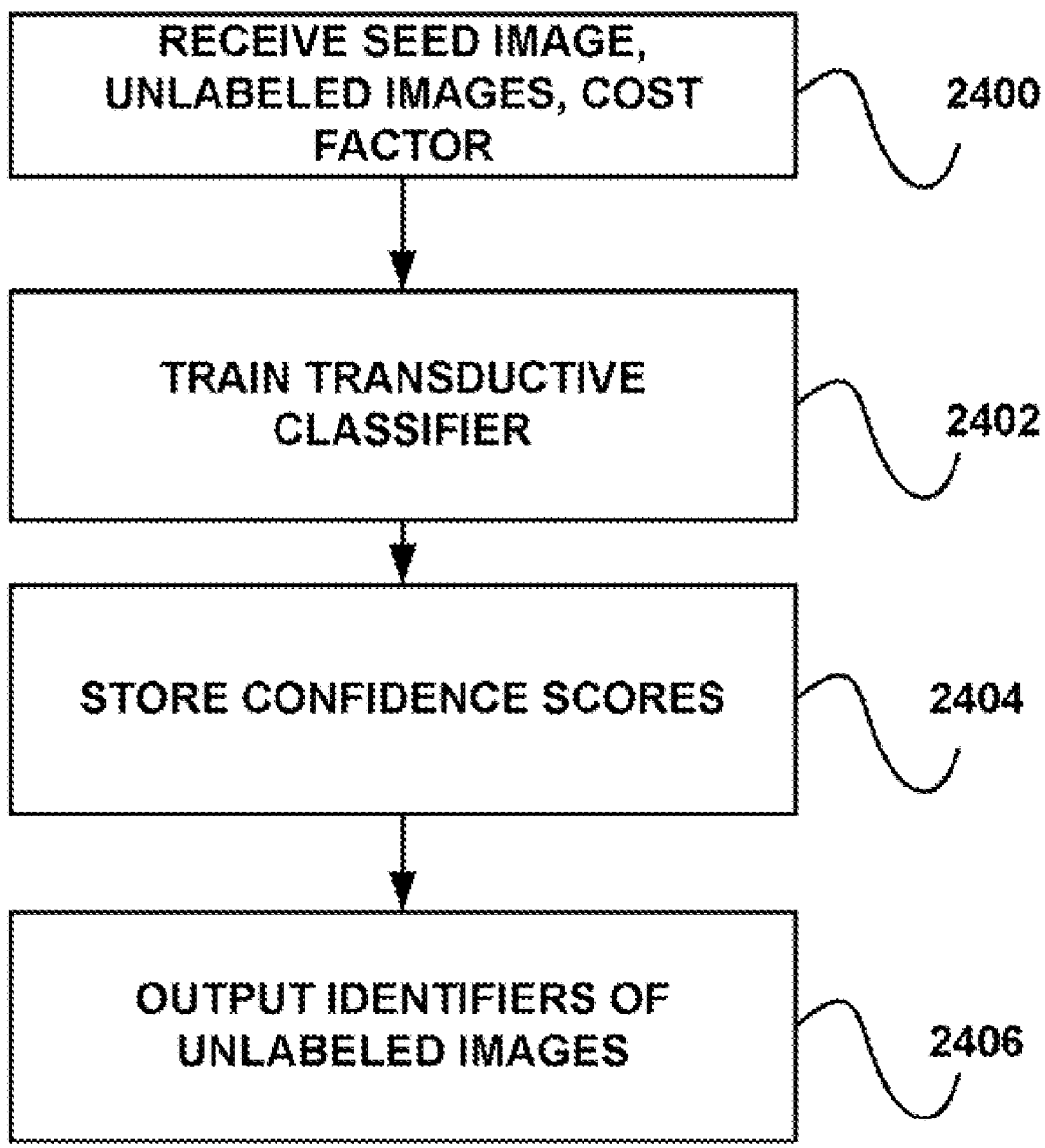
FIG. 24 illustrates, in a flowchart, a classification process performed by in accordance with one embodiment.

In yet another embodiment, a method for face recognition is presented in FIG. 24. In step 2400, at least one labeled seed image of a face is received, the seed image having a known confidence level. The at least one seed image may have a label indicative of whether the image is included in a designated category. Additionally, in step 2400 unlabeled images are received, e.g. from the police department, government agency, lost child database, airport security, or any other location, and at least one predetermined cost factor are received. Also, in step 2402 a transductive classifier is trained through iterative calculation using the at least one predetermined cost factor, the at least one seed image, and the unlabeled images, wherein for each iteration of the calculations the cost factor is adjusted as a function of an expected label value. After at least some of the iterations, in step 2404 confidence scores are stored for the unlabeled seed images.

Further, in step 2406 identifiers of the unlabeled documents having the highest confidence scores are output to at least one of a user, another system, and another process. The identifiers may be electronic copies of the document themselves, portions thereof, titles thereof, names thereof, file names thereof, pointers to the documents, etc. Also, confidence scores may be stored after each of the iterations, wherein an identifier of the unlabeled images having the highest confidence score after each iteration is output. Additionally, a data point label prior probability for the labeled and unlabeled image may be received, wherein for each iteration of the calculations the data point label prior probability may be adjusted according to an estimate of a data point class membership probability. Further, a third unlabeled image of a face, e.g., from the above airport security example, may be received, the third unlabeled image may be compared to at least some of the images having the highest confidence scores, and an identifier of the third unlabeled image may be output if a confidence that the face in the third unlabeled image is the same as the face in the seed image.

Yet another embodiment of the present invention enables a user to improve their search results by providing feedback to the document discovery system. For example, when performing a search on an internet search engine, patent or patent application search product, etc., users may get a multitude of results in response to their search query. An embodiment of the present invention enables the user to review the suggested results from the search engine and inform the engine of the relevance of one ore more of the retrieved results, e.g. "close, but not exactly what I wanted," "definitely not," etc. As the user provides feedback to the engine, better results are prioritized for the user to review.

Figure 25:
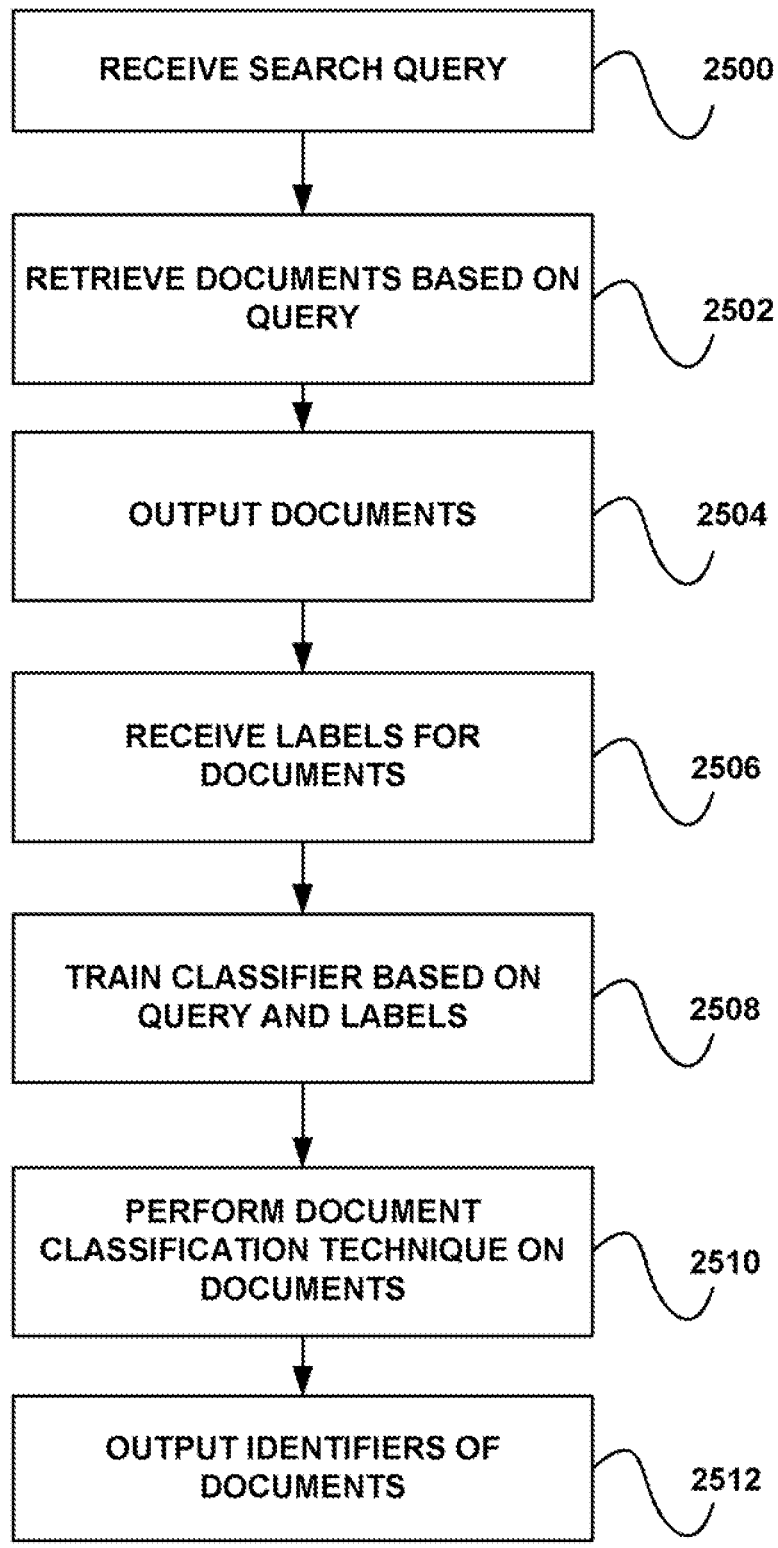
FIG. 25 illustrates, in a flowchart, a classification process performed by in accordance with one embodiment.

In one embodiment, a method for document searching is presented in FIG. 25. In step 2500, a search query is received. The search query may be any type of query, including case-sensitive queries, Boolean queries, approximate match queries, structured queries, etc. In step 2502, documents based on the search query are retrieved. Additionally, in step 2504 the documents are output, and in step 2506 user-entered labels for at least some of the documents are received, the labels being indicative of a relevance of the document to the search query. For example, the user may indicate whether a particular result returned from the query is relevant or not. Also, in step 2508 a classifier is trained based on the search query and the user-entered labels, and in step 2510 a document classification technique is performed on the documents using the classifier for reclassifying the documents. Further, in step 2512 identifiers of at least some of the documents are output based on the classification thereof. The identifiers may be electronic copies of the document themselves, portions thereof, titles thereof, names thereof, file names thereof, pointers to the documents, etc. The reclassified documents may also be output, with those documents having a highest confidence being output first.

The document classification technique may include any type of process, e.g. a transductive process, a support vector machine process, a maximum entropy discrimination process, etc. Any inductive or transductive technique described above may be used. In a preferred approach, the classifier may be a transductive classifier, and the transductive classifier may be trained through iterative calculation using at least one predetermined cost factor, the search query, and the documents, wherein for each iteration of the calculations the cost factor may be adjusted as a function of an expected label value, and the trained classifier may be used to classify the documents. In addition, a data point label prior probability for the search query and documents may be received, wherein for each iteration of the calculations the data point label prior probability may be adjusted according to an estimate of a data point class membership probability.

A further embodiment of the present invention may be used for improving ICR/OCR, and speech recognition. For example, many embodiments of speech recognition programs and systems require the operator to repeat a number of words to train the system. The present invention can initially monitor the voice of a user for a preset period of time to gather "unclassified" content, e.g., by listening in to phone conversations. As a result, when the user starts training the recognition system, the system utilizes transductive learning to utilize the monitored speech to assist in building a memory model.

Figure 26:
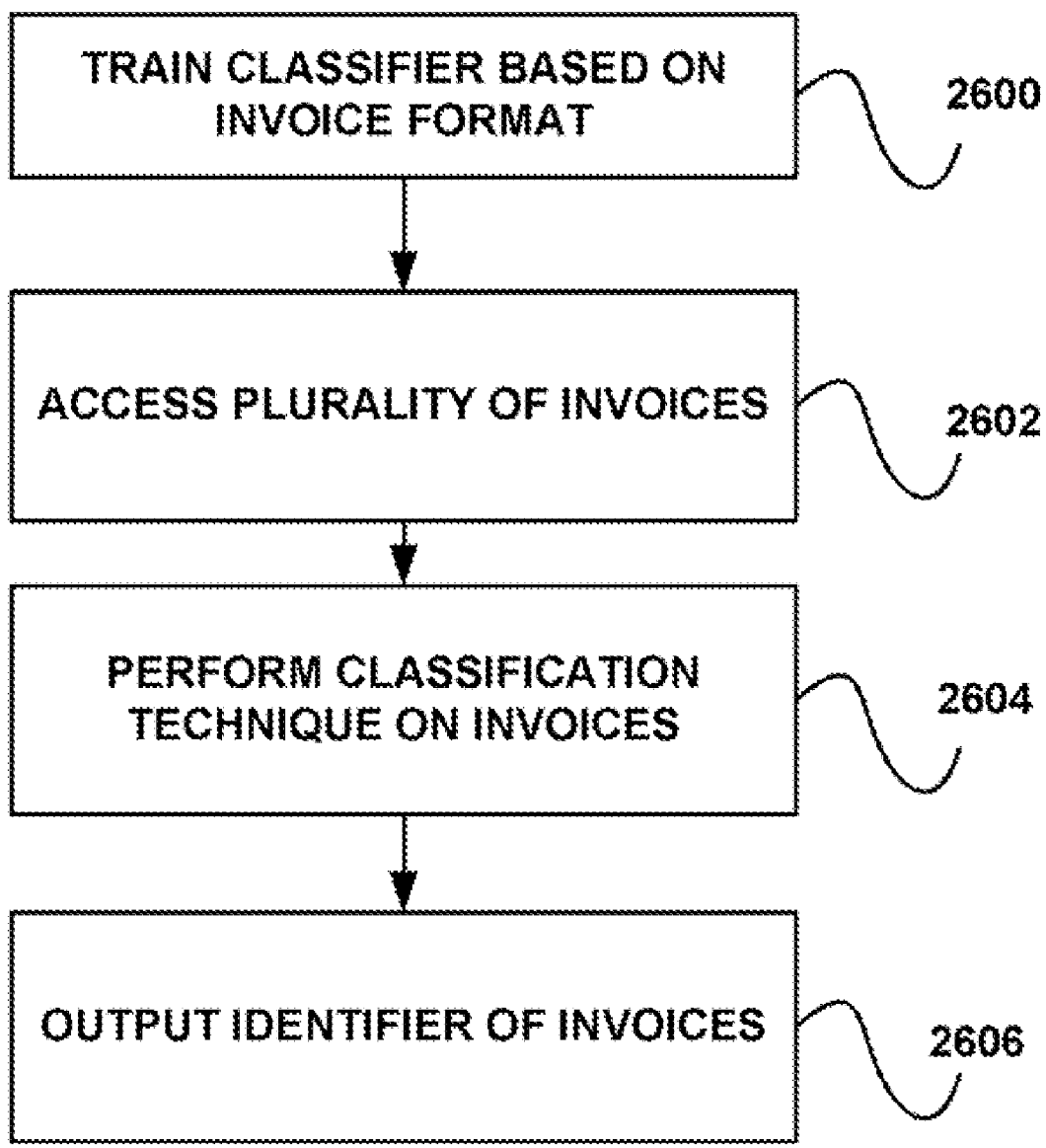
FIG. 26 illustrates, in a flowchart, a classification process performed by in accordance with one embodiment.

In yet another embodiment, a method for verifying an association of an invoice with an entity is presented in FIG. 26. In step 2600, a classifier is trained based on an invoice format associated with a first entity. The invoice format may refer to either or both of the physical layout of markings on the invoice, or characteristics such as keywords, invoice number, client name, etc. on the invoice. In addition, in step 2602 a plurality of invoices labeled as being associated with at least one of the first entity and other entities are accessed, and in step 2604 a document classification technique is performed on the invoices using the classifier. For example, any inductive or transductive technique described above may be used as a document classification technique. For example, the document classification technique may include a transductive process, support vector machine process, a maximum entropy discrimination process, etc. Also, in step 2606 an identifier of at least one of the invoices having a high probability of not being associated with the first entity is output.

Further, the classifier may be any type of classifier, for example, a transductive classifier, and the transductive classifier may be trained through iterative calculation using at least one predetermined cost factor, at least one seed document, and the invoices, wherein for each iteration of the calculations the cost factor is adjusted as a function of an expected label value, and using the trained classifier to classify the invoices. Also, a data point label prior probability for the seed document and invoices may be received, wherein for each iteration of the calculations the data point label prior probability is adjusted according to an estimate of a data point class membership probability.

One of the benefits afforded by the embodiments depicted herein is the stability of the transductive algorithm. This stability is achieved by scaling the cost factors and adjusting the label prior probability. For example, in one embodiment a transductive classifier is trained through iterative classification using at least one cost factor, the labeled data points, and the unlabeled data points as training examples. For each iteration of the calculations, the unlabeled date point cost factor is adjusted as a function of an expected label value. Additionally, for each iteration of the calculations the data point label prior probability is adjusted according to an estimate of a data point class membership probability.

The workstation may have resident thereon an operating system such as the Microsoft Windows® Operating System (OS), a MAC OS, or UNIX operating system. It will be appreciated that a preferred embodiment may also be implemented on platforms and operating systems other than those mentioned. A preferred embodiment may be written using JAVA, XML, C, and/or C++ language, or other programming languages, along with an object oriented programming methodology. Object oriented programming (OOP), which has become increasingly used to develop complex applications, may be used.

The above application uses transductive learning to overcome the problem of very sparse data sets which plague inductive face-recognition systems. This aspect of transductive learning is not limited to this application and may be used to solve other machine-learning problems that arise from sparse data.

Those skilled in the art could devise variations that are within the scope and spirit of the various embodiments of the invention disclosed herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A method for classifying documents, comprising:
   receiving at least one labeled seed document having a known confidence level of label assignment;
   receiving unlabeled documents;
   receiving at least one predetermined cost factor;
   training a transductive classifier through iterative calculation using the at least one predetermined cost factor, the at least one seed document, and the unlabeled documents, wherein for each iteration of the calculations the cost factor is adjusted as a function of an expected label value;
   after at least some of the iterations, storing confidence scores for the unlabeled documents; and
   outputting identifiers of the unlabeled documents having the highest confidence scores to at least one of a user, another system, and another process.

2. The method of claim 1, wherein the at least one seed document has a list of keywords.

3. The method of claim 1, wherein confidence scores are stored after each of the iterations, wherein an identifier of the unlabeled document having the highest confidence score after each iteration is output to the at least one of a user, another system, and another process.

4. The method of claim 1, further comprising receiving a data point label prior probability for the labeled and unlabeled documents, wherein for each iteration of the calculations the data point label prior probability is adjusted according to an estimate of a data point class membership probability.

5. A method for analyzing documents associated with legal discovery, comprising:
   receiving documents associated with a legal matter;
   performing a document classification technique on the documents using a transductive classifier trained through iterative calculation using at least one predetermined cost factor, and at least one seed document, wherein for each iteration of the calculations the cost factor is adjusted as a function of an expected label value; and
   outputting identifiers of at least some of the documents based on the classification thereof.

6. The method of claim 5, wherein the document classification technique includes a transductive process.

7. The method of claim 6, further comprising training a transductive classifier through iterative calculation using at least one predetermined cost factor, at least one seed document, and the documents associated with the legal matter, wherein for each iteration of the calculations the cost factor is adjusted as a function of an expected label value, and using the trained classifier to classify the received documents.

8. The method of claim 7, further comprising receiving a data point label prior probability for labeled and unlabeled documents, wherein for each iteration of the calculations the data point label prior probability is adjusted according to an estimate of a data point class membership probability.

9. The method of claim 5, wherein the document classification technique includes a support vector machine process.

10. The method of claim 5, wherein the document classification technique includes a maximum entropy discrimination process.

11. The method of claim 5, further comprising outputting a representation of links between the documents.

12. A method for cleaning up data, comprising:
    receiving a plurality of labeled data items;
    selecting subsets of the data items for each of a plurality of categories;
    setting an uncertainty for the data items in each subset to about zero;
    setting an uncertainty for the data items not in the subsets to a predefined value that is not about zero;
    training a transductive classifier through iterative calculation using the uncertainties, the data items in the subsets, and the data items not in the subsets as training examples;
    applying the trained classifier to each of the labeled data items to classify each of the data items; and
    outputting a classification of the input data items, or derivative thereof, to at least one of a user, another system, and another process.

13. The method of claim 12, wherein the subsets are selected at random.

14. The method of claim 12, wherein the subsets are selected and verified by a user.

15. The method of claim 12, further comprising changing the label of at least some of the data items based on the classification.

16. The method of claim 12, wherein identifiers of data items having a confidence level below a predefined threshold after classification thereof are output to a user.

17. A method for verifying an association of an invoice with an entity, comprising;
    training a classifier based on an invoice format associated with a first entity, wherein the classifier is a transductive classifier, and further comprising training the transductive classifier through iterative calculation using at least one predetermined cost factor, at least one seed document, and the invoices, wherein for each iteration of the calculations the cost factor is adjusted as a function of an expected label value;
    accessing a plurality of invoices labeled as being associated with at least one of the first entity and other entities;
    performing a document classification technique on the invoices using the classifier; and
    outputting an identifier of at least one of the invoices having a high probability of not being associated with the first entity.

18. The method of claim 17, wherein the document classification technique includes a transductive process.

19. The method of claim 17, further comprising receiving a data point label prior probability for the seed document and invoices, wherein for each iteration of the calculations the data point label prior probability is adjusted according to an estimate of a data point class membership probability.

20. The method of claim 17, wherein the document classification technique includes a support vector machine process.

21. The method of claim 17, wherein the document classification technique includes a maximum entropy discrimination process.

22. A method for managing medical records, comprising:
    training a classifier based on a medical diagnosis, wherein the classifier is a transductive classifier, and further comprising training the transductive classifier through iterative calculation using at least one predetermined cost factor, at least one seed document, and the medical records, wherein for each iteration of the calculations the cost factor is adjusted as a function of an expected label value;
    accessing a plurality of medical records;

performing a document classification technique on the medical records using the classifier; and outputting an identifier of at least one of the medical records having a low probability of being associated with the medical diagnosis.

23. The method of claim 22, wherein the document classification technique includes a transductive process.

24. The method of claim 22, further comprising receiving a data point label prior probability for the seed document and medical records, wherein for each iteration of the calculations the data point label prior probability is adjusted according to an estimate of a data point class membership probability.

25. The method of claim 22, wherein the document classification technique includes a support vector machine process.

26. The method of claim 22, wherein the document classification technique includes a maximum entropy discrimination process.

27. A method for face recognition, comprising:

receiving at least one labeled seed image of a face, the seed image having a known confidence level;

receiving unlabeled images;

receiving at least one predetermined cost factor;

training a transductive classifier through iterative calculation using the at least one predetermined cost factor, the at least one seed image, and the unlabeled images, wherein for each iteration of the calculations the cost factor is adjusted as a function of an expected label value;

after at least some of the iterations, storing confidence scores for the unlabeled seed images; and outputting identifiers of the unlabeled images having the highest confidence scores to at least one of a user, another system, and another process.

28. The method of claim 27, wherein the at least one seed image has a label indicative of whether the image is included in a designated category.

29. The method of claim 27, wherein confidence scores are stored after each of the iterations, wherein an identifier of the unlabeled images having the highest confidence score after each iteration is output.

30. The method of claim 27, further comprising receiving a data point label prior probability for the labeled and unlabeled image, wherein for each iteration of the calculations the data point label prior probability is adjusted according to an estimate of a data point class membership probability.

31. The method of claim 27, further comprising receiving a third unlabeled image of a face, comparing the third unlabeled image to at least some of the images having the highest confidence scores, and outputting an identifier of the third unlabeled image if a confidence that the face in the third unlabeled image is the same as the face in the seed image.

* * * * *

UNITED STATES PATENT AND TRADEMARK OFFICE
CERTIFICATE OF CORRECTION

PATENT NO. : 7,958,067 B2
APPLICATION NO. : 11/752673
DATED : July 12, 2011
INVENTOR(S) : Schmidtler et al.

It is certified that error appears in the above-identified patent and that said Letters Patent is hereby corrected as shown below:

col. 6, line 38 replace "Y^t" with --Y'--;
col. 6, line 55 replace "institute" with --Institute--;
col. 10, line 30 replace "Y^t" with --Y'--;
col. 11, line 47 replace "$\Theta(\lambda)=$" with --$_M(\lambda)=$-- (where the 'M' is subscript);
col. 15, line 22 replace "pb(b))," with --$p_O(b))$,-- (where the 'O' is subscript);
col. 17, line 20 replace "λt'" with --$\lambda_t$,-- (where the 't' is subscript);
col. 18, line 3 replace "λtb" with --$\lambda_t$-- (where the t is subscript);
col. 18, line 3, change "=0,δ" to normal case (not subscript).

Signed and Sealed this
Seventeenth Day of July, 2012

David J. Kappos
*Director of the United States Patent and Trademark Office*